(12) United States Patent
Bozik et al.

(10) Patent No.: US 11,612,589 B2
(45) Date of Patent: *Mar. 28, 2023

(54) COMPOSITIONS AND METHODS FOR TREATING CONDITIONS RELATED TO ELEVATED LEVELS OF EOSINOPHILS AND/OR BASOPHILS

(71) Applicant: Areteia Therapeutics, Inc., Chapel Hill, NC (US)

(72) Inventors: Michael E. Bozik, Pittsburgh, PA (US); Gregory Hebrank, Greensburg, PA (US); Wildon Farwell, Wayland, MA (US); Thomas Petzinger, Jr., Pittsburgh, PA (US); Steven Dworetzky, Jefferson Hills, PA (US)

(73) Assignee: Areteia Therapeutics, Inc., Chapel Hill, NC (US)

( * ) Notice: Subject to any disclaimer, the term of this patent is extended or adjusted under 35 U.S.C. 154(b) by 172 days.

This patent is subject to a terminal disclaimer.

(21) Appl. No.: 16/950,973

(22) Filed: Nov. 18, 2020

(65) Prior Publication Data

US 2021/0267949 A1  Sep. 2, 2021

Related U.S. Application Data

(63) Continuation of application No. 15/923,650, filed on Mar. 16, 2018, now Pat. No. 11,026,928, which is a (Continued)

(51) Int. Cl.
*A61K 31/428* (2006.01)
*A61K 45/06* (2006.01)

(52) U.S. Cl.
CPC ............ *A61K 31/428* (2013.01); *A61K 45/06* (2013.01); *Y02A 50/30* (2018.01)

(58) Field of Classification Search
CPC .... A61K 31/428; A61K 45/06; Y02A 50/422; Y02A 50/411; A61P 9/00; A61P 7/00;
(Continued)

(56) References Cited

U.S. PATENT DOCUMENTS 3,598,122 A  8/1971 Zaffaroni
3,598,123 A  8/1971 Zaffaroni
(Continued)

FOREIGN PATENT DOCUMENTS

AU   2002360600 B2   11/2007
AU   2006279643 B2   6/2010
(Continued)

OTHER PUBLICATIONS

Piercey et al. "Excitation of type II anterior caudate neurons by stimulation of dopamine $D_3$ receptors" 1997, Brain Research 762:19-28.
(Continued)

*Primary Examiner* — Savitha M Rao
*Assistant Examiner* — Andrew P Lee
(74) *Attorney, Agent, or Firm* — DLA Piper LLP

(57) ABSTRACT

Disclosed herein are methods of treating conditions, which may be associated with elevated levels of eosinophils and/or basophils, with a therapeutically effective amount of dexpramipexole or pharmaceutical acceptable salt thereof.

128 Claims, 6 Drawing Sheets

Related U.S. Application Data continuation of application No. 14/904,058, filed as application No. PCT/US2014/046380 on Jul. 11, 2014, now Pat. No. 10,828,284, which is a continuation-in-part of application No. PCT/US2013/054804, filed on Aug. 13, 2013, and a continuation-in-part of application No. 13/966,229, filed on Aug. 13, 2013, now Pat. No. 9,468,630.

(60) Provisional application No. 61/987,117, filed on May 1, 2014, provisional application No. 61/865,118, filed on Aug. 12, 2013, provisional application No. 61/859,158, filed on Jul. 26, 2013, provisional application No. 61/845,944, filed on Jul. 12, 2013.

(58) Field of Classification Search
CPC .......... A61P 43/00; A61P 37/08; A61P 35/02; A61P 33/10; A61P 33/06; A61P 31/10; A61P 21/02; A61P 17/00; A61P 13/08; A61P 11/06; A61P 11/02; A61P 11/00; A61P 1/16; A61P 1/04; A61P 1/02; A61P 1/00
See application file for complete search history.

(56) References Cited

U.S. PATENT DOCUMENTS

| | | |
|---|---|---|
| 3,731,683 A | 5/1973 | Zaffaroni |
| 3,797,494 A | 3/1974 | Zaffaroni |
| 4,031,894 A | 6/1977 | Urquhart et al. |
| 4,144,317 A | 3/1979 | Higuchi et al. |
| 4,201,211 A | 5/1980 | Chandrasekaran et al. |
| 4,286,592 A | 9/1981 | Chandrasekaran |
| 4,314,557 A | 2/1982 | Chandrasekaran |
| 4,327,725 A | 5/1982 | Cortese et al. |
| 4,379,454 A | 4/1983 | Campbell et al. |
| 4,395,859 A | 8/1983 | Rohrer |
| 4,435,180 A | 3/1984 | Leeper |
| 4,559,222 A | 12/1985 | Enscore et al. |
| 4,568,343 A | 2/1986 | Leeper et al. |
| 4,573,995 A | 3/1986 | Chen et al. |
| 4,588,580 A | 5/1986 | Gale et al. |
| 4,612,008 A | 9/1986 | Wong et al. |
| 4,626,539 A | 12/1986 | Aungst et al. |
| 4,645,502 A | 2/1987 | Gale et al. |
| 4,698,062 A | 10/1987 | Gale et al. |
| 4,704,282 A | 11/1987 | Campbell et al. |
| 4,725,272 A | 2/1988 | Gale |
| 4,731,374 A | 3/1988 | Griss et al. |
| 4,781,924 A | 11/1988 | Lee et al. |
| 4,783,337 A | 11/1988 | Wong et al. |
| 4,788,062 A | 11/1988 | Gale et al. |
| 4,806,341 A | 2/1989 | Chien et al. |
| 4,816,258 A | 3/1989 | Nedberge et al. |
| 4,843,086 A | 6/1989 | Griss et al. |
| 4,849,226 A | 7/1989 | Gale |
| 4,886,812 A | 12/1989 | Griss et al. |
| 4,904,475 A | 2/1990 | Gale et al. |
| 4,908,027 A | 3/1990 | Enscore et al. |
| 4,917,895 A | 4/1990 | Lee et al. |
| 4,938,759 A | 7/1990 | Enscore et al. |
| 4,943,435 A | 7/1990 | Baker et al. |
| 5,004,610 A | 4/1991 | Osborne et al. |
| 5,024,843 A | 6/1991 | Kuczynski et al. |
| 5,069,909 A | 12/1991 | Sharma et al. |
| 5,071,656 A | 12/1991 | Lee et al. |
| 5,082,668 A | 1/1992 | Wong et al. |
| 5,091,190 A | 2/1992 | Kuczynski et al. |
| 5,112,842 A | 5/1992 | Zierenberg et al. |
| 5,122,382 A | 6/1992 | Gale et al. |
| 5,141,750 A | 8/1992 | Lee et al. |
| 5,284,660 A | 2/1994 | Lee et al. |
| 5,314,694 A | 5/1994 | Gale et al. |
| 5,342,623 A | 8/1994 | Enscore et al. |
| 5,411,740 A | 5/1995 | Lee et al. |
| 5,442,117 A | 8/1995 | Stahly et al. |
| 5,545,413 A | 8/1996 | Kuczynski et al. |
| 5,591,454 A | 1/1997 | Kuczynski et al. |
| 5,635,203 A | 6/1997 | Gale et al. |
| 5,650,420 A | 7/1997 | Hall et al. |
| 5,674,895 A | 10/1997 | Guittard et al. |
| 5,719,060 A | 2/1998 | Hutchens et al. |
| 5,792,664 A | 8/1998 | Chait et al. |
| 5,804,215 A | 9/1998 | Cubbage et al. |
| 5,830,497 A | 11/1998 | Yamanaka et al. |
| 5,840,754 A | 11/1998 | Guittard et al. |
| 5,912,268 A | 6/1999 | Guittard et al. |
| 6,043,251 A | 3/2000 | Douillet et al. |
| 6,156,777 A | 12/2000 | Hall et al. |
| 6,187,802 B1 | 2/2001 | Cheetham et al. |
| 6,197,339 B1 | 3/2001 | Ju |
| 6,228,398 B1 | 5/2001 | Devane et al. |
| 6,255,329 B1 | 7/2001 | Maj |
| 6,262,115 B1 | 7/2001 | Guittard et al. |
| 6,284,774 B1 | 9/2001 | Wright et al. |
| 6,294,790 B1 | 9/2001 | Weinberger |
| 6,443,976 B1 | 9/2002 | Flower et al. |
| 6,458,820 B1 | 10/2002 | Hall et al. |
| 6,480,820 B1 | 11/2002 | Clopton et al. |
| 6,541,486 B1 | 4/2003 | Bitler et al. |
| 6,618,138 B2 | 9/2003 | Khoury |
| 6,667,329 B1 | 12/2003 | Maj |
| 6,675,104 B2 | 1/2004 | Paulse et al. |
| 6,727,367 B2 | 4/2004 | Pospisilik |
| 6,730,325 B2 | 5/2004 | Devane et al. |
| 6,750,235 B1 | 6/2004 | Rosenbaum |
| 6,776,984 B1 | 8/2004 | Schwartz |
| 6,793,936 B2 | 9/2004 | Devane et al. |
| 6,902,742 B2 | 6/2005 | Devane et al. |
| 6,919,092 B2 | 7/2005 | Guittard et al. |
| 6,919,373 B1 | 7/2005 | Lam et al. |
| 6,927,036 B2 | 8/2005 | Gallop et al. |
| 6,929,801 B2 | 8/2005 | Klose et al. |
| 6,930,129 B2 | 8/2005 | Lam et al. |
| 7,005,255 B2 | 2/2006 | Kaddurah-Daouk et al. |
| 7,157,480 B2 | 1/2007 | Bennett, Jr. |
| 7,344,733 B2 | 3/2008 | Beier et al. |
| 7,572,596 B2 | 8/2009 | Bowser |
| 7,741,490 B2 | 6/2010 | Castaldi et al. |
| 8,017,598 B2 | 9/2011 | Bozik et al. |
| 8,186,890 B2 | 5/2012 | Lu |
| 8,192,091 B2 | 6/2012 | Hsu et al. |
| 8,408,815 B2 | 4/2013 | Lin et al. |
| 8,445,474 B2 | 5/2013 | Bozik et al. |
| 8,518,926 B2 | 8/2013 | Bozik et al. |
| 8,519,148 B2 | 8/2013 | Raje et al. |
| 8,524,695 B2 | 9/2013 | Bozik et al. |
| 9,468,630 B2 | 10/2016 | Bozik et al. |
| 9,512,096 B2 | 12/2016 | Chen et al. |
| 9,642,840 B2 | 5/2017 | Bozik et al. |
| 9,662,313 B2 | 5/2017 | Bozik et al. |
| 9,763,918 B2 | 9/2017 | Bozik et al. |
| 9,849,116 B2 | 12/2017 | Bozik et al. |
| 9,956,206 B2 | 5/2018 | Bozik et al. |
| 10,028,940 B2 | 7/2018 | Bozik et al. |
| 10,179,774 B2 | 1/2019 | Raje et al. |
| 10,195,183 B2 | 2/2019 | Bozik et al. |
| 10,208,003 B2 | 2/2019 | Chen et al. |
| 10,383,856 B2 | 8/2019 | Bozik et al. |
| 10,383,857 B2 | 8/2019 | Bozik et al. |
| 10,980,783 B2 | 4/2021 | Bozik et al. |
| 2002/0004058 A1 | 1/2002 | Yoshii et al. |
| 2002/0103240 A1 | 8/2002 | Pospisilik |
| 2002/0106731 A1 | 8/2002 | Ruben et al. |
| 2002/0151526 A1 | 10/2002 | Gallop et al. |
| 2002/0177626 A1 | 11/2002 | Cook et al. |
| 2003/0013120 A1 | 1/2003 | Patz et al. |
| 2003/0049318 A1 | 3/2003 | Davis et al. |
| 2003/0166696 A1 | 9/2003 | Warsinsky et al. |
| 2003/0203055 A1 | 10/2003 | Rao et al. |
| 2004/0014721 A1 | 1/2004 | Hensley et al. |
| 2004/0031667 A1 | 2/2004 | Dinkel et al. |
| 2004/0033530 A1 | 2/2004 | Awrey et al. |

(56) References Cited

U.S. PATENT DOCUMENTS

| | | |
|---|---|---|
| 2004/0067991 A1 | 4/2004 | Greig et al. |
| 2004/0097540 A1 | 5/2004 | Peters et al. |
| 2004/0122104 A1 | 6/2004 | Hirsh et al. |
| 2004/0132788 A1 | 7/2004 | Chabrier De Lassauniere et al. |
| 2004/0132826 A1 | 7/2004 | Hirsh et al. |
| 2004/0219213 A1 | 11/2004 | Burnside et al. |
| 2004/0247656 A1 | 12/2004 | Beier et al. |
| 2004/0265370 A1 | 12/2004 | Odidi et al. |
| 2005/0031667 A1 | 2/2005 | Patel et al. |
| 2005/0032856 A1 | 2/2005 | Bennett |
| 2005/0053649 A1 | 3/2005 | Chalmers |
| 2005/0059717 A1 | 3/2005 | van Eupen et al. |
| 2005/0070715 A1 | 3/2005 | Bhat et al. |
| 2005/0074865 A1 | 4/2005 | Afeyan et al. |
| 2005/0089575 A1 | 4/2005 | Friedl et al. |
| 2005/0148026 A1 | 7/2005 | Bowser et al. |
| 2005/0208156 A1 | 9/2005 | Ploch et al. |
| 2005/0220877 A1 | 10/2005 | Patel et al. |
| 2005/0226926 A1 | 10/2005 | Amidon et al. |
| 2005/0265379 A1 | 12/2005 | Rao |
| 2006/0009659 A1 | 1/2006 | Maywald et al. |
| 2006/0046967 A1 | 3/2006 | Satyam |
| 2006/0051419 A1 | 3/2006 | Friedl et al. |
| 2006/0069263 A1 | 3/2006 | Gribun et al. |
| 2006/0099257 A1 | 5/2006 | Langridge et al. |
| 2006/0106224 A1 | 5/2006 | Gupta et al. |
| 2006/0110450 A1 | 5/2006 | Eisenreich |
| 2006/0121619 A1 | 6/2006 | Bowser |
| 2006/0128643 A1 | 6/2006 | Kaddurah-Daouk et al. |
| 2006/0141037 A1 | 6/2006 | Mehta et al. |
| 2006/0281797 A1 | 12/2006 | Bennett |
| 2006/0286167 A1 | 12/2006 | Staunton et al. |
| 2007/0087410 A1 | 4/2007 | Lanahan et al. |
| 2007/0105918 A1 | 5/2007 | Bennett, Jr. |
| 2007/0203209 A1 | 8/2007 | Bartolini et al. |
| 2007/0259930 A1 | 11/2007 | Bozik et al. |
| 2008/0014259 A1 | 1/2008 | Bozik et al. |
| 2008/0020028 A1 | 1/2008 | Shevchuk et al. |
| 2008/0026043 A1 | 1/2008 | Mueller et al. |
| 2008/0081041 A1 | 4/2008 | Nemeth |
| 2008/0096939 A1 | 4/2008 | Keil et al. |
| 2008/0194832 A1 | 8/2008 | Silva Guisasola et al. |
| 2008/0200505 A1 | 8/2008 | Perry et al. |
| 2008/0227985 A1 | 9/2008 | Raje et al. |
| 2008/0234338 A1 | 9/2008 | Bennett Jr. |
| 2009/0042956 A1 | 2/2009 | Bozik et al. |
| 2009/0054504 A1 | 2/2009 | Bozik et al. |
| 2009/0105483 A1 | 4/2009 | Balicki et al. |
| 2009/0149518 A1 | 6/2009 | Nishii et al. |
| 2010/0291073 A1 | 11/2010 | Koike et al. |
| 2010/0292149 A1 | 11/2010 | Bowser |
| 2011/0009460 A1 | 1/2011 | Gribkoff et al. |
| 2011/0020339 A1 | 1/2011 | Hargreave et al. |
| 2011/0190356 A1 | 8/2011 | Bozik et al. |
| 2011/0218222 A1 | 9/2011 | Bennett, Jr. |
| 2011/0224268 A1 | 9/2011 | Bozik et al. |
| 2011/0293718 A1 | 12/2011 | Bozik et al. |
| 2011/0301210 A1 | 12/2011 | Bennett, Jr. |
| 2012/0134929 A1 | 5/2012 | McGrath et al. |
| 2012/0142715 A1 | 6/2012 | Kim |
| 2012/0148575 A1 | 6/2012 | Koike et al. |
| 2012/0225915 A1 | 9/2012 | Bozik et al. |
| 2012/0253047 A1 | 10/2012 | Allegrini et al. |
| 2012/0258994 A1 | 10/2012 | McKinney et al. |
| 2013/0059801 A1 | 3/2013 | Milne et al. |
| 2013/0079526 A1 | 3/2013 | Greenfield et al. |
| 2013/0116292 A1 | 5/2013 | Bennett, Jr. |
| 2013/0123312 A1 | 5/2013 | Bozik et al. |
| 2013/0172394 A1 | 7/2013 | Bennett, Jr. |
| 2013/0230569 A1 | 9/2013 | Bozik et al. |
| 2013/0245081 A1 | 9/2013 | Gribkoff et al. |
| 2013/0273557 A1 | 10/2013 | Gribkoff et al. |
| 2013/0310430 A1 | 11/2013 | Bozik et al. |
| 2014/0018343 A1 | 1/2014 | Romero et al. |
| 2014/0031401 A1 | 1/2014 | Bozik et al. |
| 2014/0100372 A1 | 4/2014 | Raje et al. |
| 2014/0329869 A1 | 11/2014 | Bozik et al. |
| 2015/0018397 A1 | 1/2015 | Bozik et al. |
| 2015/0126745 A1 | 5/2015 | Chen et al. |
| 2015/0246119 A1 | 9/2015 | Pirozzi et al. |
| 2016/0022647 A1 | 1/2016 | Bozik et al. |
| 2016/0030397 A1 | 2/2016 | Bozik et al. |
| 2016/0158205 A1 | 6/2016 | Bozik et al. |
| 2016/0193186 A1 | 7/2016 | Bozik et al. |
| 2016/0193187 A1 | 7/2016 | Bozik et al. |
| 2016/0354350 A1 | 12/2016 | Bozik et al. |
| 2017/0158648 A1 | 6/2017 | Chen et al. |
| 2017/0281604 A1 | 10/2017 | Bozik et al. |
| 2017/0281605 A1 | 10/2017 | Bozik et al. |

FOREIGN PATENT DOCUMENTS

| | | |
|---|---|---|
| AU | 2007333050 B2 | 8/2013 |
| CA | 2605078 A1 | 10/2006 |
| CA | 2619217 A1 | 2/2007 |
| CN | 1308533 A | 8/2001 |
| CN | 1617720 A | 5/2005 |
| CN | 1735604 A | 2/2006 |
| CN | 101677564 A | 3/2010 |
| CN | 102160865 A | 8/2011 |
| CN | 102772404 A | 11/2012 |
| EP | 0186087 B1 | 8/1989 |
| EP | 0558861 A1 | 9/1993 |
| EP | 1453505 A4 | 1/2007 |
| EP | 2156833 A1 | 2/2010 |
| EP | 2305252 A1 | 4/2011 |
| EP | 2465500 A1 | 6/2012 |
| EP | 2497472 A1 | 9/2012 |
| EP | 2497473 A1 | 9/2012 |
| EP | 2497474 A1 | 9/2012 |
| EP | 2542541 A1 | 1/2013 |
| EP | 2442655 A4 | 4/2013 |
| EP | 2246053 B1 | 9/2013 |
| JP | H07504655 A | 5/1995 |
| JP | H10510809 A | 10/1998 |
| JP | 2006143708 A | 6/2006 |
| JP | 2009504748 A | 2/2009 |
| JP | 2010031059 A | 2/2010 |
| JP | 4500543 B2 | 7/2010 |
| JP | H11515012 | 5/2011 |
| JP | 6115377 B2 | 6/2017 |
| RU | 199324834 U1 | 8/2002 |
| RU | 2009126742 A | 1/2011 |
| WO | 1993017683 A1 | 9/1993 |
| WO | 1993024834 A1 | 12/1993 |
| WO | 1996018395 A1 | 6/1996 |
| WO | 1997015304 A1 | 5/1997 |
| WO | 1998059360 A1 | 4/1999 |
| WO | 2001013902 A2 | 3/2001 |
| WO | 2001022820 A1 | 4/2001 |
| WO | 2001062249 A1 | 8/2001 |
| WO | 2003049705 A2 | 1/2004 |
| WO | 2004002520 A1 | 1/2004 |
| WO | 2003070188 A2 | 2/2004 |
| WO | 2004010999 A1 | 2/2004 |
| WO | 2004041797 A1 | 5/2004 |
| WO | 2004026246 A2 | 7/2004 |
| WO | 2004058163 A2 | 10/2004 |
| WO | 2005011687 A1 | 2/2005 |
| WO | 2004050034 A2 | 4/2005 |
| WO | 2005092871 A2 | 12/2005 |
| WO | 2005123193 A2 | 3/2006 |
| WO | 2006043532 A1 | 4/2006 |
| WO | 2006012277 A2 | 8/2006 |
| WO | 2006003471 A2 | 9/2006 |
| WO | 2006015943 A2 | 2/2007 |
| WO | 2006015944 A2 | 2/2007 |
| WO | 2007022182 A1 | 2/2007 |
| WO | 2007045620 A1 | 4/2007 |
| WO | 2006076681 A2 | 6/2007 |
| WO | 2007075095 A1 | 7/2007 |
| WO | 2007076062 A2 | 7/2007 |
| WO | 2006116369 A2 | 8/2007 |
| WO | 2007137071 A2 | 11/2007 |

(56) References Cited

FOREIGN PATENT DOCUMENTS

| | | | |
|---|---|---|---|
| WO | 2007090882 A2 | 12/2007 | |
| WO | 2008023027 A2 | 2/2008 | |
| WO | 2008041240 A1 | 4/2008 | |
| WO | 2008052953 A1 | 5/2008 | |
| WO | 2008074033 A1 | 6/2008 | |
| WO | 2008113003 A1 | 9/2008 | |
| WO | 2008113056 A2 | 9/2008 | |
| WO | 2007121188 A2 | 11/2008 | |
| WO | 2008104847 A2 | 2/2009 | |
| WO | 2010022140 A1 | 2/2010 | |
| WO | 2010148409 A1 | 12/2010 | |
| WO | 2011109596 A1 | 9/2011 | |
| WO | 2011150221 A2 | 2/2012 | |
| WO | 2012019015 A3 | 5/2012 | |
| WO | 2013034550 A1 | 3/2013 | |
| WO | 2013096816 A1 | 6/2013 | |
| WO | 2013096870 A1 | 6/2013 | |
| WO | 2014134569 A1 | 2/2014 | |
| WO | 2014134569 A1 | 9/2014 | |
| WO | 2015006708 A1 | 1/2015 | |
| WO | 2015023786 A1 | 2/2015 | |
| WO | 2015023790 A1 | 2/2015 | |
| WO | 2015061777 A1 | 4/2015 | |

OTHER PUBLICATIONS

Piercey et al. "Inhibition of dopamine neuron firing by pramipexole, a dopamine D.sub.3 receptor-prefering agonist: comparison to other dopamine receptor agonists" 1996, European J. of Pharmac. 312:35-44.
Public Statement on Mirapex, Sudden Onset of Sleep from the European Agency for the Evaluation of Medicinal Products (EMEA), Jul. 19, 1999, www.emea.europa.eu/pds/human/press/pus/2064299.pdf.
Ranganathan et al, "Proteomic profiling of cerebrospinal fluid identifies biomarkers for amyotrophic lateral sclerosis" 2005, J Neurochem. 29:1461-1471.
Ranganathan et al. "PI4 Protein Profiling of Amyotrophic Lateral Sclerosis (ALS) by Mass Spectrometric Analysis" 2002 ALS and other Motor Neuron Disorders 3(2):57.
Robberecht "Oxidative Stress in Amyotrophic Lateral Sclerosis" 2000, J. Neurol. 247(1):11-16 (abstract only).
Roca-Santiago et al. "Alzheimer's Disease and Age-related Macular Degeneration" Feb. 2006, Arch. Soc. Esp. Oftalmol. 81 (2):73-78.
Rothenberg et al. "Treatment of Patients with Hypereosinophilic Syndrome with Mepolizumab" Mar. 20, 2008, The New England Journal of Medicine 358(12):1215-1228.
Rothstein et al. "Beta-Lactam antibiotics offer neuroprotection by increasing glutamate transporter expression" 2005, Nature 433(7021):73-77.
Rowland et al. "Amyotrophic Lateral Sclerosis" May 2001, N Eng Journal of Medicine, 344:1688-1700.
Rudnicki et al., "Dexpramipexole effects on functional decline and survival in subjects with amyotrophic lateral sclerosis in a Phase II study: Subgroup analysis of demographic and clinical characteristics", Feb. 1, 2013, Amyotrophic LateralSclerosis and Frontotemporal Degeneration, vol. 14, pp. 44-51.
Ryberg et al. "Discovery and Verification of Amyotrophic Lateral Sclerosis Biomarkers by Proteomics" Jul. 2010, Muscle & Nerve 42(1):104-111.
Samson et al. "Long-Term Outcomes of 118 Patients with Eosinophilic Granulomatosis with Polyangiitis (Churge-Strauss Syndrome) Enrolled in Two Prospective Trials" 2013, J. of Autoimmunity 43:60-69.
Sanchez et al. "Cystatin C as a potential cerebrospinal fluid marker for the diagnosis of Creutzfeldt-Jakob disease" 2004, Proteomics 4(8):2229-2233.
Sayeed et al. "Patch Clamp Reveals Powerful Blockade of the Mitochondrial Permeability Transition Pore by the D2-Receptor Agonist Pramipexole" 2006, FASB Journal 20:556-558.
Schilling et al. "Neuroendocrine and side effect profile of pramipexole, a new dopamine receptor agonist, in humans" 1992, Clin. Pharmacol. Ther. 51:541-548.
Schmidt et al. "Neurodegenerative diseases of the retina and potential for protection and recovery" Jun. 2008 (printed from http://www.nncbi.nim,nih.gov/pubmed/19305795?dopt.sub.-Abstract) Curr. Neuropharmacol. 6(2) (Abstract only).
Schneider et al. "Dopamine Autoreceptor Agonists: Resolution and Pharmacological Activity of 2,6-Diaminotetrahydrobenzothiazole and an Aminothiazole Analogue of Apomorphine" 1987, J. Med. Chem. 30:494-498.
Schuelke et al. "Myostatin Mutation Associated With Gross Muscle Hypertrophy in a Child" 2004, N. Engl. J. Med. 350:2682-2688 (Para.1).
Schwartz et al. "Current Strategies in the Management of Hypereosinophilic Syndrome, Including Mepolizumab" Jun. 21, 2010, Current Medical Research and Opinion 26(8):1933-1946.
Shannon et al. "Efficacy of Pramipexole, a Novel Dopamine Agonist, as Monotherapy in Mild to Moderate Parkinson's Disease" 1997, Neurology 49(3)a;724-728.
Sousa et al. "Deposition of transthyretin in early stages of familial amyloidotic polyneuropathy: evidence for toxicity of nonfibrillar aggregates" Dec. 2001, Am J Pathol. 159(6):1993-2000.
Sousa et al. "Evidence for early cytotoxic aggregates in transgenic mice for human transthyretin Leu55Pro" Nov. 2002, Am. J. of Pathol. 161(5):1935-1948.
Stein et al. "Neutralization of transthyretin reverses the neuroprotective effects of secreted amyloid precursor protein (APP) in APPsw mice resulting in tau phosphorylation and loss of hippocampal neurons: Support for the amyloid ypothesis" Sep. 1, 2004, J. Neurosci. 24(35):7707-7717.
The Foundation Fighting Blindness "Animal Models for Studying Inherited Degenerative Retinal Disease" 2000 (printed from www.retina-international.org/sci-news/animmod.doc on Jan. 11, 2009) The Foundation Fighting Blindness (23 pages).
Tobran-Tink et al. "Neuroprotection in Macular Degeneration" 2005, Age-Related Macular Degeneration: A Comprehensive Textbook (Lippincott Williams & Wilkins), 29:335-336.
Tsuzuki et al. "Structure of the Human Prealbumin Gene" Oct. 5, 1984, J. Biol. Chem. 260(22):12224-12227.
U.S. Dept. of HHS FDA CDER (Guidance for Industry), Jul. 2005, 30 pp.
Uemichi et al. "A New Mutant Transthyretin (Arg 10) Associated with Familial Amyloid Polyneuropathy" 1992, J. Med. Genet. 29:888-891.
Valent et al. "Contemporary Cnsensus Proposal on Criteria and Classification of Eosinophilic Disorders and Related Syndromes" 2012, J. Allergy Clin. Immunol. 130:607-612.
Voskoglou-Nomikos et al., "Clinical Predictive Value of the in Vitro Cell Line, Human Xenograft, and Mouse Allograft Preclinical Cancer Models", Clinical Cancer Research (Sep. 15, 2003), 9:4227-4239.
Wang et al. "R+ pramipexole as a mitochondrially focused neuroprotectant: initial early phase studies in ALS" Feb. 2008, Amyotroph Lateral Scler. 9(1):50-58.
Wedi et al. "Chronic urticarial serum induces histamine release, leukotriene production, and basophil CD63 surface expression-inhibitory effects of anti-inflammatory drugs" Journal of allegery and clinical immunology, Mar. 2000, 105(3):552-560.
Winkler et al. "Oxidative damage and age-related macular degeneration" Nov. 3, 1999, Mol. Vis. 5:32 (Abstract only).
Wong "A 384-well cell-based phosphor-ERK assay for dopamine D2 and D3 receptors" 2004, Analytical Biochem. 333:265-272.
Wong et al. "Activation of Extracellular Signal-Regulated Kinase by Dopamine D2 and D3 Receptors" 2003, Society for Neuroscience Abstracts (retrieved on line at sfn.scholarone.com/itin2003/main.html?new.sub.-page.sub.-id=126&abstrac-t.sub.--id=3866&p.sub.-num=363.4&is.sub.-tech= on Jun. 23, 2008).
Worker "Novel Therapeutic Strategies" 1999, IDrugs, Current Drugs Ltd. GB 2(9):848-852.
Wright et al. "Influence of Probenecid (PR) and Cimetidine (C) on Pramipexole (PX) Pharmacokinetics" Feb. 1995, Clin. Pharmacol. & Ther. 59(2):PII-99 (abstract only).

(56) References Cited

OTHER PUBLICATIONS

Zheng et al. "Purification and identification of an estrogen binding protein from rat brain: oligomycin sensitivity-conferring protein (OSCP), a subunit of mitochondrial F0F1-ATP synthase/ATPase" Jan. 1999, J. Ster. Biochem. Mol. Biol.68(1-2):65-75.
Abrahamson et al. "Structure and expression of the human cystatin C gene" 1990, Biochem J. 268(2):287-294.
Abramova et al. "Inhibition by R(+) or S(−) Pramipexole of Caspase Activation and Cell Death Induced by Methylpyridinium Ion or Beta Amyloid Peptide in SH-SY5Y Neuroblastoma" 2002, J. Neuroscience Res. 67(4):494-500.
Agardh et al. "Expression of antioxidant enzymes in rat retinal ischemia followed by reperfusion" Jul. 2006, Metabolism 55(7):892-898 (Abstract).
Aguila et al. "Prognosis in Amyotrophic Lateral Sclerosis: A population based study" 2003, Neurology 60:813-819.
Akintola-Ogunremi et al. "Chronic lymphocytic leukemia presenting with symptomatic centeral nervous system involvement" 2002, Ann. Hematol. 81:402-404.
Anonymous "Variant of Parkinson's Drug Tested in ALS" Jul. 19, 2006 (printed from v1/v1/w.als mda.org/researc!1 /news/0607•19als Qramii;;:exole.html on 2121108 ) (Abstract).
Anosova et al. "Antigenecity and Immunogenicity of Allogeneic Retinal Transplants" Oct. 2001, J. Clin. Invest. 108(8):1175-1183.
Ansel et al. "Pharmaceutical Dosage Forms and Drug Delivery Systems, 61; n; ed." 1995, Williams and Wilkins Media, Malvern, PA (TOC).
Anthony et al. "Protective Immune Mechanisms in Helminth Infection" Dec. 2007, Nat Rev Immunol. 7(12):975-987.
Arico et al. Restless Legs Syndrome as the Presenting Symptom of Multiple Myeloma 2013, Journal of Clinical Sleep Medicine 9(4):383-385.
Arrimal et al. "Eosinophilic and ubiquitinated neuronal inclusions in motor and extra-motor cortices in a brain with amyotrophic lateral sclerosis" Brain Pathology (1997) 1074.
Asgeirsson et al. "Hereditary cystatin C amyloid angiopathy: monitoring the presence of the Leu-68-7Gln cystatin C variant in cerebrospinal fluids and monocyte cultures by MS" 1998, Biochem. J, 329 (Pt 3):497-503 (1998).
Ashcroft et al. "An Efficient and Scalable Synthesis of the Endothelin Antagonists UK-350,926 and UK-349,862 Using a Dynamic Resolution Process" 2005, Organic Proc. Res. & Dev. 9:663-669.
Balicki et al. "A New, Efficient and Economic Method for Preparation of Pramipexole" May 16, 2006, Book of Abstracts: The Fifth Multidisciplinary conference on Drug Research, Pielaszek Research (Warszawa, Poland) Poster No. 1-19, p. 30 (English Abstract).
Balicki et al. "New method for preparing pramipexole dihydrochloride monohydrate" 2006, Przemysl Chemiczny 85(5):344-346.
Banker et al. "Modern Pharmaceutics" 1979, Marcel Dekker, Inc. (TOC).
Beal "Oxidative Metabolism" 2000, Ann. N.Y. Acad. Sci. 924:164-169.
Beatty et al. "The Role of Oxidative Stress in the Pathogenesis of Age-Related Macular Degeneration" 2000, Surv. Opthalmol 45(2):115-134.
Benson et al. "Identification of carriers of a variant plasma prealbumin (transthyretin) associated with familial amyloidotic polyneuropathy type J" 1985,; J. Clin. Invest. 74:71-75.
Berge et al., Pharmaceutical Salts, 1977, J. Pharm. Sciences 66(1):1-19.
Bergen et al. "Identification of transthyretin variants by sequential proteomic and genomic analysis" 2004, Clin. Chem. 50(9):1544-1552.
Bernstein et al. "Transythyretin: Its response to malnutrition and stress injury. Clinical usefulness and economic implications" Dec. 2002, Clin. Chem. Lab. Med. 40(12):1344-1348.
Biglan et al. "A Review of Pramipexole and its Clinical Utility in Parkinson's Disease" 2002, Expert Opinion Pharmacotherapy 3(2):197-210.

Borchelt et al. "Superoxide dismutase 1 with mutations linked to familial amyotrophic lateral sclerosis possesses significant activity" 1994, PNAS USA 91(17):8292-8296.
Bozik et al. "Phase 2 Study of the Safety, Tolerability and Clinical Effects of KNS 760704 in ALS Subjects" Dec. 2009, 20th International Symposium on ALS/MND Abstract C40.
Bozik et al. "Safety, Tolerability, and Pharmacokinetics of KNS-760704 (Dexpramipexole) in Healthy Adult Subjects" 2011, J. Clin. Pharmacol. 51:1177-1185.
Brooks "EI Escorial rld Federation of Neurology Criteria for the Diagnosis of Amyotrophic Lateral Sclerosis" 1994, Journal of the Neurlogical Sciences 124(Suppl.):96-107.
Brooks et al. "EI Escorial revisited: Revised criteria for the diagnosis of amotrophic lateral sclerosis" 2000, ALS and other motor neuron disorders 1:293-299.
Butterfield et al. "Treatment of Hypereosinophilic Syndromes—The First 100 Years" Apr. 2012, Seminars in Hematology 49(2):182-191.
Carvey, et al. "Attenuation of levodopa-induced toxicity in mesencephalic cultures by pramipexole" 1997, J. Neural. Transm. 209-228.
Cassarino et al. "An evaluation of the role of mitochondria in neurodegenerative diseases: mitochondrial mutations and oxidative pathology, protective nuclear responses, and cell death in neurodegeneration" 1999, Brain Res. Rev. 29:1-25.
Cassarino et al. "Cyclosporin A increases resting mitochondrial membrane potential in SY5Y cells and reverses the depressed mitochondrial membrane potential of Alzheimer's disease cybrids" May 13, 1998, Biochem. and Biophysical Research Comm.248:168-173.
Cassarino et al. "Interaction among mitochondria, mitogen-activated protein kinases, and nuclear factor-kappaB in cellular models of Parkinson's disease" Apr. 2000, J Neurochem 74(4):1384-92.
Cassarino et al. "Pramipexole reduces reactive oxygen species production in vivo and in vitro and inhibits the mitochondrial permeability transition produced by the parkinsonian neurotoxin methylpyridinium ion" 1998, J. Neurochem. 71(1):295-301.
Cleveland et al. "From Charcot to Lou Gehrig: deciphering selective motor neuron death in ALS" Nov. 2001, Nature 2:806-819.
Corcoran et al. "Absence of retinoids can induce motoneuron disease in the adult rat and a retinoid defect is present in motoneuron disease patients" 2002, J. Cell. Sci. 115:4735-4741.
Corrigan et al. "Comparison of Pramipexole, Fluoxetine, and Placebo in Patients with Major Depression" 2000, Depression and Anxiety 11:58-65.
Cudkowicz et al. "Dexpramipexole versus placebo for patients with amyotrophic lateral sclerosis (EMPOWER): a ramdomised double-blind phase 3 trial" 2013, Lancet Neurol. 12:1059-1067.
Cudkowicz et al. "Measures and Markers in Amyotrophic Lateral Sclerosis" 2004, NeuroRx: The Journal of the American Society for Experimental Neuro Therapeutics 1(2):273-283.
Cudkowicz et al. "The effects of dexpramipexole (KNS-760704) in individuals with amyotrophic lateral sclerosis" 2011 Nature Medicine 17:1652-1656.
Danzeisen et al. "Targeted Antioxidative and Neuroprotective Properties of the Dopamine Agonist Pramipexole and Its Nondopaminergic Enantiomer SND919CL2x [(+)2-Amino-4, 5, 6, 7-tetrahydro-6-L-propylamino-benzothiazole Dihydrochloride]" 2006, J. Pharmacol. Exp. Ther. 316:189-199.
Davis et al. "Eosinophils and Cancer" Aug. 20, 2014, Cancer Immunol Res. 2(1):1-8.
Declaration of James P. Bennett Under 37 C.F.R. 1.132 dated Dec. 15, 2009.
Deigner et al. "Apoptosis Modulators in the Therapy of Neurodegenerative Diseases" Apr. 2000, Ex. Opin. Investigational Drugs 9(4):747-764.
Deng et al. "Elevation of cystatin C in susceptible neurons in Alzheimer's disease" Sep. 2001, Am. J. Pathol. 159(3):1061-1068.
Dooley et al. "Pramipexole. A Review of its Use in the Managemetn of Early and Advanced Parkinson's Disease" Jun. 1998, Drugs Aging 12(6):495-514. (abstract only).
Drobny et al. "Possible Extrapyramidal System Degradation in Parkinson's Disease" 2000, Brain Research Bulletin 53(4):425-430.

(56) References Cited

OTHER PUBLICATIONS

Dulohery et al. "Lung Involvement in Hypereosinophilic Syndromes" 2011, Respiratory Medicine 105:114-121.

EMA Public Summary of Opinion on Orphan Designation, Feb. 4, 2015, European Medicines Agency.

Email correspondence from James P. Bennett to Michael Bozik dated Apr. 6, 2007 with a draft manuscript entitled "R(+) Pramipexole as a Neuroprotectant I: Effects of R(+) Pramipexole Treatment of ALS on ALSFRSr Forced Vital Capacity and Neurophysiological Index".

International Search Report for PCT/US2002/039970 dated Jul. 17, 2003.

Jacques et al. "Enantiomers, Racemates and Resolutions" 1981, John Wiley and Sons, Inc., New York (TOC).

Johnson et al. "Relationships between drug activity and NCI preclinical in vitro and in vivo models and early clinical trials" 2001, British Journal of Cancer 84(10):1424-1431.

Kamel et al. "Lead exposure and amyotrophic lateral sclerosis" May 2002, Epidemiology 13(3):311-319.

Kato et al. "A neurosphere-derived factor, cystatin C, supports differentiation of ES cells into neural stem cells" 2006, PNAS USA 103(15):6019-6024.

Khan et al. "Alzheimer's disease cybrids replicate beta-amyloid abnormalities through cell death pathways" Aug. 2000, Ann Neurol. 48(2):148-55.

Kieburtz "Safety and Efficacy of Pramipexole in Early Parkinson Disease" 1997, JAMA 278(2):125-130.

Kitamura et al. "Protective Effects of the Antiparkinsonian Drugs Talipexole and Pramipexole against 1-Methyl-4-phenylpyridinium-Induced Apoptotic Death in Human Neuroblastoma SH-Sy5Y Cells" 1998, Molecular Pharmacology 54:1046-1054.

Klion "How I Treat Hypereosinophilic Syndroms" Oct. 29, 2009, Blood 114(18):3736-3741.

Lahortiga et al. "Activity of imatinib in systemic mastocytosis with chronic basophilic leukemia and a PRKG2-PDGFRB fusion" 2008, Haematological/The Hematology Journal 93(1): 51-56.

Le et al. "Antioxidant property of pramipexole independent of dopamine receptor activation in neuroprotection" 2000, J. Neural. Transm. 107(10):1165-73.

Lee et al. "Carcinogenicity Predictions for a Group of 30 Chemicals Undergoing Rodent Cancer Bioassays Based on Rules Derived from Subchronic Organ Toxicities" 1996, Environmental Health Perspectives 104(5):1059-1063.

Levy et al. "Stroke in Icelandic Patients With Hereditary Amyloid Angiopathy is Related to a Mutation in the Cystatin C Gene, An Inhibitor of Cysteine Proteases" 1989, The Journal of Experimental Medicine 169(5):1771-1778.

Liang et al. "Oxidative stress-induced mitochondrial DNA damage in human retinal pigment epithelial cells: a possible mechanism for RPE aging and age-related macular degeneration" 2003, Exp. Eye Res. 76(4):397-403.

Lieberman et al. "Clinical evaluation of pramipexole in advanced Parkinson's disease: Results of a double-blind, placebo-controlled, parallel-group study" 1997, Neurology 49:162-168.

Lieberman et al. "Pharmaceutical Dosage Forms: Disperse Systems" 1996, Marcel Dekker, Inc., New York vol. 2 (TOC).

Lieberman et al. "Pharmaceutical Dosage Forms: Tablets" 1989 Marcel Dekker Inc. New York vol. 1 (TOC).

Lin et al. "Large-scale protein identification using mass spectrometry" 2003, Biochimica et Biophysica Acta 16460-2):1-10.

Liou et al. "Case Report Churg-Strauss syndrome presented as multiple intracerebral hemorrhage" (1997) Lupis 6:279-282.

Liu et al. "Eosinophil-Derived Neurotoxin Is Elevated in Patients with Amyotrophic Lateral Sclerosis" Feb. 21, 2013, Mediators of Inflammation 2013:1-7.

Lofberg, et al. "Immunohistochemical characterization of the amyloid deposits and quantitation of pertinent cerebrospinal fluid proteins in hereditary cerebral hemorrhage with amyloidosis" 1987, Stroke 18(2):431-440.

Lomen-Hoerth "Amyotrophic lateral sclerosis from bench to bedside" 2008, Semin. Neurol. 28(2):205-211.

Love "Oxidative Stress in Brain Ischemia" Apr. 5, 1999, Brain Pathology 9(1)119-131 (Abstract only).

Lucchinetti et al. "Inflammatory Cortical Demyelination in Eady Multiple Sclerosis" 2011, The New England Journal of Medicine 365:2188-2197.

Malaspina et al. "Differential expression of 14 genes in amyotrophic lateral sclerosis spinal cord detected using gridded eDNA arrays" 2001, J. Neurochemistry 77(1):132-145.

Martens "Cloning and Sequence Analysis of Human Pituitary eDNA Encoding the Novel Polypeptide 7B2" 1988, FEBS Letters 234(1):160-164.

Martens et al. "The novel pituitary polypeptide 7B2 is a highly-conserved protein coexpressed with proopiomelanocortin" Apr. 1989, Eur. J. Biochem. 181(1):75-79.

Masi et al. "The American College of Rheumatology 1990 Criteria for the Classification of Churg-Strauss Syndrome (Allergic Granulomatosis and Angiitis)" Aug. 1990, Arthritis Rheum. 33(8):1094-1100.

Matthews et al. "Assessment of the Health Effects of Chemicals in Humans: I. Qsar Estimation of the Maximum Recommended Therapeutic Dose (MRTD) and No Effect Level (NOEL) of Organic Chemicals Based on Clinical Trial Data" 2004, Current DrugDiscovery Technologies 1:61-76.

Mbikay et al. "Neuroendocrine secretory protein 7B2: structure, expression and functions" Jul. 15, 2001, Biochem J. 357(2):329-342.

Menzies et al. "Mitochondrial dysfunction in a cell culture model of familial amyotrophic lateral sclerosis" Jul. 2002, Brain 125(7):1522-1533.

Mepolizumab, Orphan Drug Designations and Approvals, downloaded Nov. 20, 2018, FDA, 2 page abstract (https://www.accessdata.fda.gov/scripts/opdlistng/oopd/detailedindex.cfm?cfgridkey=182103).

Merck Manuals Online Medical Library, Age-Related Macular Degeneration (ARMD), 2005, printed Aug. 13, 2008 from http://www.merck.com/mmpe/print/sec09/ch106/ch106b.html, 2 pages.

Mey et al. "Retinoic Acid Signaling in the Nervous System of Adult Vertebrates" 2004, The Neuroscientist 10(5):409-421.

Mhatre et al. "Oxidative Stress and Neuroinflammation in Alzheimer's Disease and Amyotrophic Lateral Sclerosis; Common Links and Potential Therapeutic Targets" Apr. 2004, J. Alzheimers Dis. 6(2):147-157 (abstract only).

Mierau at al., Pramipexole binding and activation of cloned and expressed dopamine D.sub.2, D.sub.3 and D.sub.4 receptors, 1995, Eur. J. Pharmacol. 290:29-36.

Miklya et al. "A pharmacological analysis elucidating why, in contrast to (-)-deprenyl (selegiline), .alpha.-tocopherol was ineffective in the DATATOP study" 2003, Life Sciences 72:2641-2648.

MIRAPEX® Prescribing Information from Boehringer Ingelheim 2006 http:www.biopsychiatry.compramipexole-mirapex.pdf <http://www.biopsychiatry.com/pramipexole-mirapex.pdf> (retrieved May 10, 2012).

Moore et al. "An Efficient and Operationally Convenient General Synthesis of Tertiary Amines by Direct Alkylation of Secondary Amines with Alkyl Halides in the Presence of Huenig's Base" 2005, ARKIVOC 6:287-292.

Nagai et al., "Rats Expressing Human Cytosolic Copper-Zinc Superoxide Dismutase Transgenes with Amyotrophic Lateral Sclerosis: Associated Mutations Develop Motor Neuron Disease," Dec. 1, 201, The Journal of Neuroscience, 21(23): 9246-9254.

National Institutes of Health/ U.S. National Library of Medicine, "Creatine phosphokinase test", Updated Jan. 9, 2015, URL of this page: //www.nlm.nih.gov/medlineplus/ency/article/003503.htm, pp. 1-4.

Nilsen et al. "Mitochondria as Therapeutic Targets of Estrogen Action in the Central Nervous System" Aug. 2004, Curr. Drug Targets—CNS & Neurol. Disorders 3(4):297-313.

Ong et al. "An Evaluation of the Use of Two-Dimensional Gel Electrophoresis in Proteomics" 2001, Biomolecular Engineering 18(5):195-205.

(56) References Cited

OTHER PUBLICATIONS

Palliative (n.d.) The American Heritage.RTM. Stedman's Medical Dictionary, Retrieved Jun. 12, 2009, from Dictionary.com website: http://dictionary.com/browse/palliative.
Panch et al. "Dexpramipexole as an Oral Steroid-Sparing Agent in Hypereosinophilic Syndromes" Aug. 2, 2018, Blood 132(5):501-509.
Paquet et al. "The neuroendocrine precursor 7B2 is a sulfated protein proteolytically processed by a ubiquitous furin-like convertase" Jul. 29, 1994, J Biol. Chem. 269(30):19279-19285.
Pattee et al. "Reduction of oxidative stress in amyotrophic lateral sclerosis following pramipexole treatment" Jan. 2003, Amyotrophic Lateral Sclerosis and Other Motor Neuron Disorders 4(2):90-95 (abstract only).
Paulson "Protein Fate in Neurodegenerative Proteinopathies: Polyglutamine Diseases Join the (Mis) Fold" 1999, Am. J. Hum. Genet. 64(2):339-345.
PDF copy regarding ALS from Florida Hospital, retrieved on Jul. 12, 2018.
Petersen et al., Impaired Mitochondria Activity in the Insulin-Resistant Offspring of Patients with Type 2 Diabetes, 2004, New England Journal of Medicine 350:664-671.
Email correspondence from James P. Bennett to Michael Bozik dated Apr. 6, 2007 with a draft manuscript entitled "R(+) Pramipexole as a Neuroprotectant II: Tolerability and Pharmacokinetics in ALS of Esclating Doses to 300mgday".
Email correspondence from James P. Bennett to Michael Bozik dated May 11, 2006 with a presentation entitled "ALS: An Investigator's View of the Disease and its Treatment".
Email correspondence from James P. Bennett to Michael Bozik dated Oct. 9, 2006 with a draft grant application.
European Seach Report and Opinion dated Aug. 1, 2012 for EP 12163888.
European Search Report and Opinion dated Aug. 2, 2012 for EP 12164060.
European Search Report and Opinion dated May 10, 2012 for EP 11186875.
European Search Report and Written Opinion dated Feb. 18, 2011 for EP 10009931.
European Search Report and Written Opinion for EP 12163947 dated Aug. 1, 2012.
European Search Report dated Mar. 2, 2011 for EP 10075571.9.
European Supplemental Search Report dated Apr. 8, 2010 for EP 08743922.
European Supplemental Search Report dated Apr. 9,2 010 for EP 08732306.9.
European Supplemental Search Report dated Nov. 23, 2006 for EP02795869.
European Supplemental Search Report dated Oct. 4, 2010 for EP 10008579.4.
Extended European Search Report and Written Opinion dated Sep. 11, 2012 for EP 12164067.
Extended European Supplemental Search Report and Written Opinion dated Feb. 18, 2011 for EP10075571.
Feher et al. "Mitochondrial alternations of retinal pigment epithelium in age- related macular degeneration" Jun. 2006, Neurobiology of Aging 27(7) (Abstract, 2 pages) (Printed from http//www.neurobiologyofaging.org/article/PIIS01974580005001545 on Dec. 11, 2009).
Ferger et al. "The dopamine agonist pramipexole scavenges hydroxyl free radicals induced by striatal application of 6-hydroxydopamine in rats: an in vivo microdialysis study" Aug. 29, 2000, Brain Research 883:216-223.
Gennaro "Remington: The Science and Practice of Pharmacy, 2om Ed." Lippincott Williams & Wilkins, Baltimore, MD, 2000, Ch. 38:704-720.
Gleevac, Highlights of Prescribing Information, Sep. 2016.

Golebiewski et al. "Application of GC/MS for Identyfication of the Sideproducts in a Process of Preparation of Pramipexole" May 16, 2006, Book of Abstracts: The Fifth Multidisciplinary conference on Drug Research, Pielaszek Research (Warszawa, Poland) Poster No. 1-57, p. 49.
Goodall et al. "Association of the H63D polymorphism in the hemochromatosis gene with sporadic ALS" 2005, Neurology 65(6):934-937.
Goodman et al. "The Pharmaceutical Basis of Therapeutics, 6.sup.th Ed." 1980, MacMillan Publishing Co., New York (TOC).
Graves et al. "Inflammation in amyotrophic lateral sclerosis spinal cord and brain is mediated by activated macrophages mast cells and T cells" Amyotrophic Lateral Sclerosis and Other Motor Neuron Disorders Official Publication of the rld Federation of Neurology Research Group on Motor Neuron Diseases Dec. 2004 5(4):213-219.
Greenwald et al. "Drug delivery systems based on trimethyl lock lactonization: poly(ethylene glycol) prodrugs of amino-containing compounds" Feb. 10, 2000 J. Med. Chem. 43(3):475-487.
Gu et al., Pramipexole protects against apoptotic cell death by non-dopaminergic mechanisms, 2004, J. Neurochem. 91:1075-1081.
Guillevin et al. "Prognostic Factors in Polyarteritis Nodosa and Churg-Strauss Syndrome: A Prospective Study in 342 Patients" 1996, Medicine 75(1):17-28.
Gurney et al. "Benefit of Vitamin E, Riluzole, and Gabapentin in a Transgenic Model of Familial Amyotrophic Lateral Sclerosis" Feb. 1996, Ann. Neurol. 39(2):147-157.
Gurney et al. "Motor Neuron Degeneration in Mice That Express a Human Cu, Zn Superoxide Dismutase Mutation" 1994, Science 264:1772-1775.
Haghikia et al. "Therapies for multiple sclerosis: translation achievements and outstanding needs" May 2013 Trends in Moleecular Medicine 19(5):309-319.
Halestrap "The Role of Mitochondria in Cell Death" Mar. 24, 2003, Endocrine Abstracts 5:513 (Abstract).
Hall et al. "Brain hydroxyl radical generation in acute experimental head injury" Feb. 1993, J. Neurochem. 60(2):588-594.
Hall et al. "Neuroprotective effects of the dopamine $D_2/D_3$ agonist pramipexole against postischemic or methamphetamine-induced degeneration of nigrostriatal neurons" Aug. 6, 1996, Brain Research 742:80-88.
Hansen et al. "First Generation Process for the Preparation of the DPP-IV Inhibitor Sitagliptin" 2005, Organic Proc. Res. & Dev. 9:634-639.
Hardy et al. "Genetic Classification of Primary Neurodegenerative Disease" Nov. 6, 1998, Science 282(5391):1075-1079.
Hasegawa et al. "A New Process for Synthesis of the Astrcyte Activation Suppressor, ONO-2506" 2005, Organic Proc. Res. & Dev. 9:774-781.
Hubble Pre-clinical Studies of Pramipexole: Clinical Relevance May 2000 Eur. J. Neurol. 7(Supp 1):15-20 (abstract only).
Initial Scientific Discussion for the Approval of Mirapex from the European Agency for the Evaluation of Medicinal Products (EMEA) 2005 www.emea.europa.eu/humandocs/PDFS/EPAR/Mirapexin/059097en6.pdf.
International Search Report and Written Opinion for PCT/US2006/031831 dated Dec. 7, 2006.
International Search Report and Written Opinion for PCT/US2007/087639 dated Apr. 7, 2007.
International Search Report and Written Opinion for PCT/US2008/057059 dated Jul. 11, 2008.
International Search Report and Written Opinion for PCT/US2008/057158 dated Jun. 29, 2009.
International Search Report and Written Opinion for PCT/US2009/054292 dated Oct. 22, 2009.
International Search Report and Written Opinion for PCT/US2010/039379 dated Aug. 25, 2010.
International Search Report and Written Opinion for PCT/US2011/038159 dated Dec. 12, 2011.
International Search Report and Written Opinion for PCT/US2013/054804 dated Mar. 21, 2014.

(56) References Cited

OTHER PUBLICATIONS

International Search Report and Written Opinion for PCT/US2014/019668 dated Jun. 9, 2014.
International Search Report and Written Opinion for PCT/US2014/046380 dated Dec. 10, 2014.
International Search Report and Written Opinion for PCT/US2014/050943 dated Nov. 6, 2014.
International Search Report and Written Opinion for PCT/US2014/050951 dated Oct. 22, 2014.
International Search Report and Written Opinion for PCT/US2016/022067 dated Jun. 3, 2016.
U.S. Appl. No. 61/267,945, filed Dec. 9, 2009 with USPTO Official Filing Receipt.
U.S. Appl. No. 61/911,984, filed Dec. 4, 2013 with USPTO Official Filing Receipt.
Knopp Biosciences and Bozik et al. "Dexpramipexole Decreases Blood Eosinophils Results of Two Clinical Trials in Patients with Amyotrophic Lateral Sclerosis" Poster presented at the 8th Biennial International Eosinophil Society Conference on Jul. 12, 2013, Oxford, United Kingdom.
Robinson "Lessons Learned—and a Roadmap to New Approaches—After Disappointing Phase 3 Results for Two Drugs for ALS" Jun. 6, 2013, Neurology Today pp. 26-27.
U.S. Appl. No. 13/987,324, filed Jan. 18, 2013 with USPTO Official Filing Receipt, Request for Conversion to Non-Provisional Application, and Decision Granting Same (U.S. Appl. No. 13/987,324).
U.S. Appl. No. 61/845,939, filed Jul. 12, 2013 with USPTO Official Filing Receipt.
U.S. Appl. No. 61/859,147, filed Jul. 26, 2013 with USPTO Official Filing Receipt.
U.S. Appl. No. 61/683,141, filed Aug. 14, 2012 with USPTO Official Filing Receipt.
U.S. Appl. No. 61/865,987, filed Aug. 14, 2013 with USPTO Official Filing Receipt.
International Patent Application No. PCT/US2013/054993 as filed Aug. 14, 2013.
Extended European Search Report and Written Opinion for EP14822432.2 dated Dec. 16, 2016.
Dworetzky et al. "The targeted eosinophil-lowering effects of dexpramipexole in clinical studies" 2017, Blood Cells, Molecules and Diseases 63:62-65.
Study to Evaluate Safety and Efficacy of Dexpramipexole (KNS-760704) in Subjects with Hypereosinophilic Syndrome Apr. 2, 2014, National Institutes of Health Clinical Center (CC) (National Institute of Allergy and Infectious Diseases (NIAID)), Verified Dec. 1, 2017 (downloaded from internet on Nov. 7, 2022), available at <https://clinicaltrials.gov/ct2/show/study/NCT02101138>.

| PARAMETER | COHORT | BASELINE | MONTH 6 | CHANGE | p-VALUE |
|---|---|---|---|---|---|
| WHITE BLOOD CELLS x$10^9$/L | PLACEBO | 6.90 | 7.2 | 4.3% | < 0.0001 |
| | TREATMENT | 6.79 | 6.01 | -11.5% | |
| EOSINOPHILS x$10^9$/L | PLACEBO | 0.133 | 0.159 | 19.5% | < 0.0001 |
| | TREATMENT | 0.133 | 0.042 | -68.4% | |
| BASOPHILS x$10^9$/L | PLACEBO | 0.045 | 0.046 | 2.2% | < 0.0001 |
| | TREATMENT | 0.044 | 0.024 | -45.5% | |
| NEUTROPHILS x$10^9$/L | PLACEBO | 4.467 | 4.794 | 7.3% | < 0.0001 |
| | TREATMENT | 4.388 | 4.024 | -8.3% | |
| LYMPHOCYTES x$10^9$/L | PLACEBO | 1.818 | 1.782 | -2.0% | < 0.0001 |
| | TREATMENT | 1.784 | 1.54 | -13.7% | |
| MONOCYTES x$10^9$/L | PLACEBO | 0.437 | 0.419 | -4.1% | < 0.0001 |
| | TREATMENT | 0.433 | 0.377 | -12.9% | |
| RED BLOOD CELLS x$10^{12}$/L | PLACEBO | 4.69 | 4.71 | 0.4% | = 0.1123 |
| | TREATMENT | 4.71 | 4.77 | 1.3% | |
| PLATELETS x$10^9$/L | PLACEBO | 255.9 | 276.6 | 8.1% | = 0.4925 |
| | TREATMENT | 250.3 | 266.9 | 6.6% | |

FIG. 5

COMPOSITIONS AND METHODS FOR TREATING CONDITIONS RELATED TO ELEVATED LEVELS OF EOSINOPHILS AND/OR BASOPHILS

CROSS-REFERENCE TO RELATED APPLICATIONS

This application is a continuation of U.S. application Ser. No. 14/904,058, filed Jan. 8, 2016, which is a U.S. national stage filing under 35 U.S.C. § 371 of International Application No. PCT/US2014/046380 filed Jul. 11, 2014, which claims priority to U.S. Provisional Application No. 61/845,944 filed Jul. 12, 2013, U.S. Provisional Application No. 61/859,158 filed Jul. 26, 2013, U.S. Provisional Application No. 61/865,118 filed Aug. 12, 2013 and U.S. Provisional Application No. 61/987,117 filed May 1, 2014. International Application No. PCT/US2014/046380 is a continuation-in-part of International Application No. PCT/US2013/054804 filed Aug. 13, 2013, which claims priority to U.S. Provisional Application No. 61/845,944 filed Jul. 12, 2013, U.S. Provisional Application No. 61/859,158 filed Jul. 26, 2013 and U.S. Provisional Application No. 61/865,118 filed Aug. 12, 2013. International Application No. PCT/US2014/046380 is a continuation-in-part of U.S. application Ser. No. 13/966,229 filed Aug. 13, 2013, issued as U.S. Pat. No. 9,468,630 on Oct. 18, 2016, which claims priority to U.S. Provisional Application No. 61/845,944 filed Jul. 12, 2013, U.S. Provisional Application No. 61/859,158 filed Jul. 26, 2013, U.S. Provisional Application No. 61/865,118 filed Aug. 12, 2013. Each of which are hereby incorporated by reference in their entireties.

SUMMARY

Embodiments of the present invention relate to methods of treating a condition in a subject in need thereof comprising administering to the subject a therapeutically effective amount of dexpramipexole or a pharmaceutically acceptable salt thereof, wherein the condition is treated. In some embodiments, the levels of eosinophils, basophils or a combination thereof in the subject is reduced following administration to the subject of a therapeutically effective amount of dexpramipexole or a pharmaceutically acceptable salt thereof.

Embodiments of the present invention relate to methods of treating a condition associated with granulocytes in a subject in need thereof comprising administering to the subject a therapeutically effective amount of dexpramipexole (also known as (6R)-4,5,6,7-tetrahydro-N6-propyl-2,6-benzothiazolediamine), or a pharmaceutically acceptable salt thereof, such as, (6R)-4,5,6,7-tetrahydro-N6-propyl-2,6-benzothiazolediamine dihydrochloride monohydrate, wherein the subject's level of granulocytes is reduced. In certain embodiments, the granulocytes are selected from eosinophils, basophils and a combination thereof.

Some embodiments are directed to methods of treating a condition characterized by elevated levels of eosinophils and/or basophils in a subject comprising administering to the subject in need thereof a therapeutically effective amount of dexpramipexole or a pharmaceutically acceptable salt thereof, wherein the level of eosinophils and/or basophils are reduced. In some embodiments, the condition is characterized by elevated levels of eosinophils and/or basophils in the peripheral blood, tissue, or a combination thereof. In some embodiments, a condition characterized by elevated levels of eosinophils is characterized by levels of eosinophils above about 300 cells per microliter in the peripheral blood. In some embodiments, a condition characterized by elevated levels of basophils is characterized by levels of basophils above about ≥100 cells per microliter in the peripheral blood.

In some embodiments, the condition is hypereosinophilic syndrome.

In some embodiments, the condition is chronic sinusitis with nasal polyps.

In some embodiments, the condition is asthma. In some embodiments, asthma is selected from atopic asthma, allergic asthma, persistent asthma, mild asthma, moderate asthma, severe asthma and combinations thereof.

In some embodiments, the therapeutically effective amount of dexpramipexole or a pharmaceutically acceptable salt thereof is from about 50 mg to about 1,500 mg per day. In some embodiments, the therapeutically effective amount is from about 100 mg to about 1,500 mg per day. In some embodiments, the therapeutically effective amount is from about 150 mg to about 1,500 mg per day. In some embodiments, the therapeutically effective amount is from about 300 mg to about 1,500 mg per day. In some embodiments, the therapeutically effective amount is from about 50 mg to about 300 mg per day. In some embodiments, the therapeutically effective amount is from about 100 mg to about 600 mg per day. In some embodiments, the therapeutically effective amount is from about 150 mg to about 600 mg per day. In some embodiments, the therapeutically effective amount is from about 300 mg to about 600 mg per day.

In some embodiments, administering a therapeutically effective amount comprises administering the daily dose as a fraction of the daily dose (as described herein) two or more times per day. In some embodiments, administering a therapeutically effective amount comprises administering a dose equal to about half of a daily dose twice per day. In some embodiments, the dose is administered every about 12 hours. In some embodiments, administering a therapeutically effective amount comprises administering about 75 mg two times per day. In some embodiments, administering a therapeutically effective amount comprises administering about 25 mg two times per day, about 75 mg two times per day, about 150 mg two times per day or about 300 mg two times per day.

Some embodiments further comprise administering to the subject a therapeutically effective amount of one or more secondary agents selected from a corticosteroid, a non-steroidal anti-inflammatory drug (NSAID), a tyrosine kinase inhibitor, a fusion protein, a monoclonal antibody directed against one or more pro-inflammatory cytokines, a chemotherapeutic agent, or a combination thereof.

Various embodiments may also comprise an induction step. In some embodiments, said induction step comprises administering to said subject a therapeutically effective amount of a secondary agent capable of decreasing levels of eosinophils and/or basophils in the subject prior to administration of a therapeutically effective amount of dexpramipexole. In some embodiments, the secondary agent is dexpramipexole. In some embodiments, the secondary agent is selected from a corticosteroid, a non-steroidal anti-inflammatory drug (NSAID), a tyrosine kinase inhibitor, a fusion protein, a monoclonal antibody directed against one or more pro-inflammatory cytokines, a chemotherapeutic agent, or a combination thereof. In some embodiments, said induction step comprises administering a therapeutically effective amount of a secondary agent for a period of about 1 day to about 6 months.

BRIEF DESCRIPTION OF THE FIGURES

In FIG. 2A the time period marked "W" represents the end of the 4-week washout following the month 3 time point.

FIG. 5 shows the change in complete blood counts (CBC) in dexpramipexole and placebo groups from baseline to month 6 in the Phase 3 trial.

DETAILED DESCRIPTION

Figure 1:
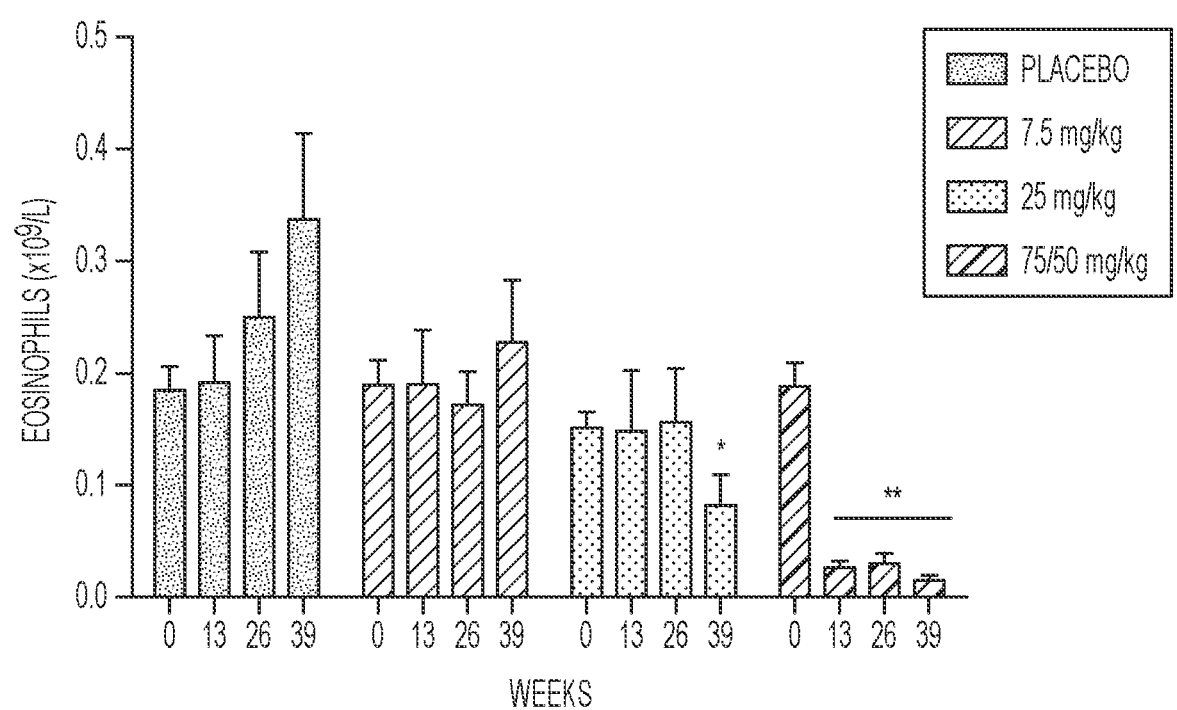
FIG. 1 depicts the dose- and time-dependent effects of dexpramipexole on eosinophil counts from minipigs. The reduction of eosinophils was observed in minipigs in long-term toxicity studies (n=5-9 dose group/treatment interval).

Granulocytes are white blood cells containing cytoplasmic granules and are generated from progenitor cells in the bone marrow. Upon certain challenges, such as allergen exposure and infection, the inflammatory response may include the stimulation of granulocyte production and their release from the bone marrow, their entry into the bloodstream, their migration to target tissues, and their release, through degranulation, of cytotoxic granules. While granulocyte recruitment and activation represents a normal and appropriate response to an inflammatory challenge, many pathological states are associated with granulocytes, including significantly elevated levels of granulocytes in the blood.

Various types of granulocytes have evolved to provide host defense mechanisms. These cellular types include eosinophils and basophils. A large number of conditions have been associated with elevated levels of eosinophils and/or basophils, individually and in combination.

As dexpramipexole was well-tolerated in humans following exposures up to 18 months, it may represent a novel therapeutic approach for the treatment of conditions associated with elevated levels of eosinophils and/or basophils.

Methods and pharmaceutical compositions to reduce levels of granulocytes could address significant and persistent unmet medical needs, including in allergic and inflammatory diseases. These conditions may be associated with elevated levels of eosinophils and/or basophils. Elevated levels of eosinophils in particular have been associated with many human and veterinary diseases.

Inflammatory and allergic conditions associated with elevated levels of eosinophils and/or basophils are treated primarily with corticosteroids. While often initially effective at ameliorating condition signs and symptoms, corticosteroids exhibit significant side effect profiles, particularly during the extended periods of administration required to treat chronic inflammatory conditions. Moreover, many subjects become refractory to corticosteroid treatment.

In some conditions associated with elevated levels of eosinophils and/or basophils, such as hypereosinophilic syndrome, subjects may require treatment with toxic chemotherapeutic or biologic agents, such as hydroxyurea and interferon α. In other conditions associated with elevated levels of eosinophils and/or basophils, such as chronic sinusitis with nasal polyps, subjects may require surgical intervention. In asthma, one of the most prevalent conditions associated with elevated levels of eosinophils and/or basophils, insufficient condition control is associated with massive loss in workplace productivity and lost school days for children.

A number of biologic therapies have been approved or remain in development for various conditions associated with elevated levels of eosinophils and/or basophils. However, these treatments generally require in-clinic administration, may cause immunological reactions, including the production of neutralizing antibodies, and may cause injection-site pain.

Accordingly, a major need exists for a small molecule agent with established preclinical and clinical safety experience for the treatment of conditions associated with elevated levels of eosinophils and/or basophils.

Dexpramipexole ((6R)-2-amino-4,5,6,7-tetrahydro-6-(propylamino) benzothiazole), is a synthetic aminobenzothiazole derivative with the following structure:

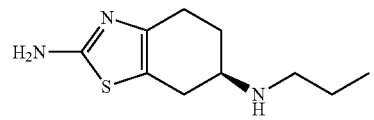

As used herein, dexpramipexole may be administered as a free base of a pharmaceutical acceptable salt. Pharmaceutical acceptable salts include, but are not limited to, any acid addition salt, preferably a pharmaceutically acceptable acid addition salt, including, but not limited to, halogenic acid salts such as hydrobromic, hydrochloric, hydrofloric and hydroiodic acid salt; an inorganic acid salt such as, for example, nitric, perchloric, sulfuric and phosphoric acid salt; an organic acid salt such as, for example, sulfonic acid salts (methanesulfonic, trifluoromethan sulfonic, ethanesulfonic, benzenesulfonic or p-toluenesufonic, acetic, malic, fumaric, succinic, citric, benzonic gluconic, lactic, mandelic, mucic, pamoic, pantothenic, oxalic and maleic acid salts; and an amino acid salt such as aspartic or glutamic acid salt. The acid addition salt may be a mono- or di-acid addition salt, such as a di-hydrohalogic, di-sulfuric, di-phosphoric or di-organic acid salt. In all cases, the acid addition salt is used as an achiral reagent which is not selected on the basis of any expected or known preference for the interaction with or precipitation of a specific optical isomer of the products of this disclosure.

Although any methods and materials similar or equivalent to those described herein can be used in the practice or testing of embodiments of the present invention, the exemplary methods, devices, and materials are now described.

In each of the embodiments described herein, the method may comprise administering a therapeutically effective amount of dexpramipexole or a pharmaceutically acceptable salt thereof. In each of the embodiments described herein, the method may consist essentially of administering a therapeutically effective amount of dexpramipexole or a pharmaceutically acceptable salt thereof. In each of the embodiments described herein, the method may consist of administering a therapeutically effective amount of dexpramipexole or a pharmaceutically acceptable salt thereof. The term "comprising" means "including, but not limited to." The term "consisting essentially of" means the method or composition includes the steps or components specifically recited, and may also include those that do not materially affect the basic and novel characteristics of the present invention. The term "consisting of" means the method or composition includes only the steps or components specifically recited.

In each of the embodiments disclosed herein, the compounds and methods may be utilized with or on a subject in need of such treatment, which may also be referred to as "in need thereof." As used herein, the phrase "in need thereof" means that the subject has been identified as having a need for the particular method or treatment and that the treatment has been given to the subject for that particular purpose.

As used herein, the term "patient" and "subject" are interchangeable and may be taken to mean any living organism, which may be treated with compounds of the present invention. As such, the terms "patient" and "subject" may include, but is not limited to, any non-human mammal, primate or human. In some embodiments, the "patient" or "subject" is an adult, child, infant, or fetus. In some embodiments, the "patient" or "subject" is a human. In some embodiments, the "patient" or "subject" is a mammal, such as mice, rats, other rodents, rabbits, dogs, cats, swine, cattle, sheep, horses, primates, or humans.

As used herein, the term "eosinophil" refers to an eosinophil granulocyte. In some embodiments, the term "eosinophil" refers to a human eosinophil progenitor (hEoP). In some embodiments, the term "eosinophil" refers to an eosinophil lineage-committed progenitor (EoP). In some embodiments, the term "eosinophil" refers to a human common myeloid progenitor (hCMP). In some embodiments, the term "eosinophil" refers to any combination of an eosinophil granulocyte, a human eosinophil progenitor (hEoP), an eosinophil lineage-committed progenitor (EoP), and a human common myeloid progenitor (hCMP). In some embodiments, the term "eosinophil" refers to a CD34+ CD125+ progenitor cell. In some embodiments, the term "eosinophil" refers to an eosinophil residing in the bone marrow, in the systemic circulatory system, and/or in organ tissues. In some embodiments, the organ tissue is the lung, the skin, the heart, the brain, the eye, the gastrointestinal tract, the thymus, the spleen, the ear, the nose or combinations thereof.

As used herein, the term "basophil" refers to a basophil granulocyte. In some embodiments, the term "basophil" refers to a human basophil progenitor. In some embodiments, the term "basophil" refers to a basophil lineage-committed progenitor. In some embodiments, the term "basophil" refers to a human common myeloid progenitor (hCMP). In some embodiments, the term "basophil" refers to any combination of an basophil granulocyte, a human basophil progenitor, a basophil lineage-committed progenitor, and a human common myeloid progenitor (hCMP). In some embodiments, the term "basophil" refers to a basophil residing in the bone marrow, in the systemic circulatory system, and/or in organ tissues. In some embodiments, the organ tissue is the lung, the skin, the heart, the brain, the eye, the gastrointestinal tract, the thymus, the spleen, the ear, the nose or combinations thereof.

As used herein, a condition characterized by elevated levels of eosinophils and/or basophils in a subject refers to a condition in which the numbers of eosinophils and/or basophils, as the case may be, are increased or raised compared with a normal subject or are increased or raised compared to another subject with the same condition.

As used herein, the terms "adjunctive administration" and "adjunctively" may be used interchangeably, and refer to simultaneous administration of more than one compound in the same dosage form, simultaneous administration in separate dosage forms, and separate administration of more than one compound as part of a single therapeutic regimen.

As used herein, the term "antibody" may be used to include antibody and antibody fragments such as, Fab, Fab', F(ab')2, scFv, dsFv, ds-scFv, dimers, minibodies, diabodies, bispecific antibody fragments, multimers, and any combination thereof, and fragments from recombinant sources and/or produced in transgenic animals. The antibody or fragment may be from any species including mice, rats, rabbits, hamsters and humans. Chimeric antibody derivatives, i.e., antibody molecules that combine a non-human animal variable region and a human constant region are also contemplated within the scope of the invention. Chimeric antibody molecules may include, for example, humanized antibodies which comprise the antigen binding domain from an antibody of a mouse, rat, or other species, with human constant regions. Conventional methods may be used to make chimeric antibodies. It is expected that chimeric antibodies would be less immunogenic in a human subject than the corresponding non-chimeric antibody.

As used herein, the term "a no observable adverse effect level" (NOAEL) dose refers to an amount of active compound or pharmaceutical agent that produces no statistically, clinically or biologically significant increases in the frequency or severity of adverse effects between an exposed population and its appropriate control; some effects may be produced at this level, but they are not considered as adverse, or as precursors to adverse effects. The exposed population may be a system, tissue, animal, individual or human being treated by a researcher, veterinarian, medical doctor, or other clinician.

Before the present compositions and methods are described, it is to be understood that this invention is not limited to the particular processes, compositions, or methodologies described, as these may vary. Moreover, the processes, compositions, and methodologies described in particular embodiments are interchangeable. Therefore, for example, a composition, dosages regimen, route of administration, and so on described in a particular embodiments may be used in any of the methods described in other particular embodiments. It is also to be understood that the terminology used in the description is for the purpose of describing the particular versions or embodiments only, and is not intended to the limit the scope of the present invention which will be limited only by the appended claims. Unless defined otherwise, all technical and scientific terms used herein have the same meanings as commonly understood by one of the ordinary skill in the art. Although any methods similar or equivalent to those describe herein can be used in the practice or testing of embodiments of the present invention, the preferred methods are now described. All publications and references mentioned herein are incorporated by reference. Nothing herein is to be construed as an admission that the invention is not entitled to antedate such disclosure by virtue of prior invention.

It must be noted that, as used herein, and in the appended claims, the singular forms "a", "an" and "the" include plural reference unless the context clearly dictates otherwise.

As used herein, the term "about" means plus or minus 10% of the numerical value of the number with which it is being used. Therefore, about 50% means in the range of 45%-55%.

"Optional" or "optionally" may be taken to mean that the subsequently described structure, event or circumstance may or may not occur, and that the described includes instances where the event occurs and instances where it does not.

"Administering" when used in conjunction with a therapeutic means to administer a therapeutic directly or indirectly into or onto a target tissue to administer a therapeutic to a patient whereby the therapeutic positively impacts the tissue to which it is targeted. "Administering" a composition may be accomplished by oral administration, injection, infusion, inhalation, absorption or by any method in combination with other known techniques. "Administering" may include the act of self-administration or administration by another person such as a health care provider.

The term "improves" is used to convey that the present invention changes either the appearance, form, characteristics, structure, function and/or physical attributes of the tissue to which it is being provided, applied or administered. "Improves" may also refer to the overall physical state of an individual to whom an active agent has been administered. For example, the overall physical state of an individual may "improve" if one or more symptoms of the disease, condition or disorder are alleviated by administration of an active agent.

As used here, the term "therapeutic" means an agent utilized to treat, combat, ameliorate or prevent an unwanted disease, condition or disorder of a patient.

The terms "therapeutically effective amount" or "therapeutic dose" is used herein are interchangeable and may refer to the amount of an active agent or pharmaceutical compound or composition that elicits a clinical, biological or medicinal response in a tissue, system, animal, individual or human that is being sought by a researcher, veterinarian, medical doctor or other clinical professional. A clinical, biological or medical response may include, for example, one or more of the following: (1) preventing a disease, condition or disorder in an individual that may be predisposed to the disease, condition or disorder but does not yet experience or display pathology or symptoms of the disease, condition or disorder, (2) inhibiting a disease, condition or disorder in an individual that is experiencing or displaying the pathology or symptoms of the disease, condition or disorder or arresting further development of the pathology and/or symptoms of the disease, condition or disorder, and (3) ameliorating a disease, condition or disorder in an individual that is experiencing or exhibiting the pathology or symptoms of the disease, condition or disorder or reversing the pathology and/or symptoms experience or exhibited by the individual.

The term "treating" may be taken to mean prophylaxis of a specific disorder, disease or condition, alleviation of the symptoms associated with a specific disorder, disease or condition and/or prevention of the symptoms associated with a specific disorder, disease or condition. In some embodiments, the term refers to slowing the progression of the disorder, disease or condition or alleviating the symptoms associated with the specific disorder, disease or condition. In some embodiments, the term refers to alleviating the symptoms associated with the specific disorder, disease or condition. In some embodiments, the term refers to alleviating the symptoms associated with the specific disorder, disease or condition. In some embodiments, the term refers to restoring function which was impaired or lost due to a specific disorder, disorder or condition.

As used herein, the terms "enantiomers," "steresiosomers," and "optical isomers may be used interchangeably and refer to molecules which contain an asymmetric or chiral center and are mirror images of one another. Further, the terms "enantiomers," "stereoisomers," or "optical isomers" describe a molecule which, in a given configuration, cannot be superimposed on its mirror images.

As used herein, the terms "optically pure" or "enantiomerically pure" may be taken to indicate that a composition contains at least 99.95% of a single optical isomer of a compound. The term "enantiomerically enriched" may be taken to indicate that a least 51% of a composition in a single optical isomer or enantiomer. The term "enantiomeric enrichment" as used herein refer to an increase in the amount of one enantiomer as compared to the other. A "racemic" mixture is a mixture of about equal amounts of (6R) and (6S) enantiomers of a chiral molecule.

Throughout this disclosure, the word "pramipexole" will refer to (6S) enantiomer of 2-amino-4,5,6,7-tetrahydro-6-(propylamino)benzothiazole unless otherwise specified.

The term "pharmaceutical composition" shall mean a composition including at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan. A pharmaceutical composition may, for example, contain dexpramipexole or a pharmaceutically acceptable salt of dexpramipexole as the active ingredient. Alternatively, a pharmaceutical composition may contain dexpramipexole or a pharmaceutically acceptable salt of dexpramipexole as the active ingredient.

"Pharmaceutically acceptable salt" is meant to indicate those salts which are, within the scope of sound medical judgment, suitable for use in contact with the tissues of a patient without undue toxicity, irritation, allergic response and the like, and are commensurate with a reasonable benefit/risk ratio. Pharmaceutically acceptable salts are well known in the art. For example, Berge et al. (1977) J. Pharm. Sciences, Vol 6. 1-19, describes pharmaceutically acceptable salts in detail. A pharmaceutical acceptable "salt" is any acid addition salt, preferably a pharmaceutically acceptable acid addition salt, including, but not limited to, halogenic acid salts such as hydrobromic, hydrochloric, hydrofloric and hydroiodic acid salt; an inorganic acid salt such as, for example, nitric, perchloric, sulfuric and phosphoric acid salt; an organic acid salt such as, for example, sulfonic acid salts (methanesulfonic, trifluoromethan sulfonic, ethanesulfonic, benzenesulfonic or p-toluenesufonic, acetic, malic, fumaric, succinic, citric, benzonic gluconic, lactic, mandelic, mucic, pamoic, pantothenic, oxalic and maleic acid salts; and an amino acid salt such as aspartic or glutamic acid salt. The acid addition salt may be a mono- or di-acid addition salt, such as a di-hydrohalogic, di-sulfuric, di-phosphoric or di-organic acid salt. In all cases, the acid addition salt is used as an achiral reagent which is not selected on the basis of any expected or known preference for the interaction with or precipitation of a specific optical isomer of the products of this disclosure.

As used herein, the term "daily dose amount" refers to the amount of dexpramipexole per day that is administered or prescribed to a patient. This amount can be administered in multiple unit doses or in a single unit does, in a single time during the day or at multiple times during the day Embodiments of the present invention relate to methods of treating a condition in a subject in need thereof comprising administering to the subject a therapeutically effective amount of dexpramipexole or a pharmaceutically acceptable salt thereof, wherein the condition is treated. In some embodiments, the levels of eosinophils, basophils or a combination thereof in the subject is reduced following administration to the subject of a therapeutically effective amount of dexpramipexole or a pharmaceutically acceptable salt thereof.

Embodiments of the present invention relate to methods of treating a condition in a subject in need thereof comprising administering to the subject a therapeutically effective amount of dexpramipexole or a pharmaceutically acceptable salt thereof, wherein the subject's level of granulocytes is reduced. In certain embodiments, the granulocytes are selected from eosinophils, basophils and a combination thereof.

Various embodiments described herein are directed to a method of treating a condition characterized by normal levels of eosinophils and/or basophils or elevated levels of eosinophils and/or basophils in a subject in need thereof comprising administering to the subject a therapeutically effective amount of dexpramipexole, or a pharmaceutically acceptable salt thereof, wherein the levels of eosinophils and/or basophils are reduced. In some embodiments, the condition is characterized by elevated levels of eosinophils and/or basophils. In some embodiments, the condition is characterized by normal levels of eosinophils and/or basophils in tissues including, but not limited to lung tissue, skin tissue, bone marrow, heart tissue, brain tissue, peripheral nerve tissue, vascular tissue, gastrointestinal tissue, ocular tissue, aural tissue, or nasal tissue and combinations thereof. In yet other embodiments, the condition is characterized by normal levels of eosinophils and/or basophils in the peripheral blood and tissues. In some embodiments, the condition is characterized by elevated levels of eosinophils and/or basophils in tissues including, but not limited to lung tissue, skin tissue, bone marrow, heart tissue, brain tissue, peripheral nerve tissue, vascular tissue, gastrointestinal tissue, ocular tissue, aural tissue, or nasal tissue and combinations thereof. In yet other embodiments, the condition is characterized by elevated levels of eosinophils and/or basophils in the peripheral blood and tissues.

In some embodiments, the condition is characterized by normal levels of eosinophils or elevated levels of eosinophils. In some embodiments, the condition is characterized by normal levels of basophils or elevated levels of basophils. In some embodiments, the condition is characterized by elevated levels of basophils with normal levels of eosinophils. In other embodiments, the condition is characterized by elevated levels of eosinophils with normal levels of basophils. In other embodiments, the condition is characterized by elevated levels of basophils and elevated levels of eosinophils. In other embodiments, the condition is characterized by normal levels of basophils and normal levels of eosinophils. In the foregoing embodiments, the normal or elevated levels of eosinophils and/or basophils (as the case may be) may be in tissues including, but not limited to lung tissue, skin tissue, bone marrow, heart tissue, brain tissue, peripheral nerve tissue, vascular tissue, gastrointestinal tissue, ocular tissue, aural tissue, or nasal tissue and combinations thereof. In the foregoing embodiments, the normal or elevated levels of eosinophils and/or basophils (as the case may be) may be in the peripheral blood and tissues.

In some embodiments, the condition is characterized by elevated levels of eosinophils and/or basophils in the peripheral blood, tissue, or a combination thereof. In some embodiments, the condition is characterized by elevated levels of eosinophils and/or basophils in tissue. In some embodiments, the condition is characterized by elevated levels of eosinophils and/or basophils in tissues including, but not limited to lung tissue, skin tissue, bone marrow, heart tissue, brain tissue, peripheral nerve tissue, vascular tissue, gastrointestinal tissue, ocular tissue, aural tissue, or nasal tissue and combinations thereof. In yet other embodiments, the condition is characterized by elevated levels of eosinophils and/or basophils in the peripheral blood and tissues.

In some embodiments, treating the condition results in a reduction of the levels of eosinophils and/or basophils. In some embodiments, the reduction of the levels of eosinophils and/or basophils is in the peripheral blood, tissue, or a combination thereof. In certain embodiments, treating the condition results in a reduction of the levels of eosinophils and/or basophils in tissues including, but not limited to, lung tissue, skin tissue, bone marrow, heart tissue, brain tissue, peripheral nerve tissue, vascular tissue, gastrointestinal tissue, ocular tissue, aural tissue, or nasal tissue and combinations thereof. In certain embodiments, the levels are reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%. In certain embodiments, the levels are reduced to normal. In certain embodiments, the levels are reduced to zero within the level of detection.

In some embodiments, a subject with normal levels of eosinophils is a subject with levels of eosinophils considered to be within the normal range or limits for the particular subject and/or condition. In some embodiments, a subject with normal levels of eosinophils is characterized by levels of eosinophils of less than about 300 cells per microliter in the peripheral blood. In some embodiments, a subject with normal levels of eosinophils is characterized by levels of eosinophils of less than about 200 cells per microliter in the peripheral blood. In some embodiments, a subject with normal levels of eosinophils is characterized by levels of eosinophils of less than about 150 cells per microliter in the peripheral blood. In some embodiments, a subject with normal levels of eosinophils is characterized by levels of eosinophils of less than about 100 cells per microliter in the peripheral blood. In some embodiments, a subject with elevated levels of eosinophils is a subject with levels of eosinophils considered to be outside of the normal range or limit for the particular subject and/or condition. In some embodiments, a condition characterized by elevated levels of eosinophils is characterized by levels of eosinophils above about 300 cells per microliter in the peripheral blood. In yet other embodiments a condition characterized by elevated levels of eosinophils is characterized by levels of eosinophils selected from above about 300 cells per microliter in the peripheral blood, about 350 cells per microliter in the peripheral blood, about 400 cells per microliter in the peripheral blood, about 450 cells per microliter in the peripheral blood, about 500 cells per microliter in the peripheral blood, about 600 cells per microliter in the peripheral blood, about 700 cells per microliter in the peripheral blood, about 800 cells per microliter in the peripheral blood, about 900 cells per microliter in the peripheral blood, about 1,000 cells per microliter in the peripheral blood, about 1,100 cells per microliter in the peripheral blood, about 1,200 cells per microliter in the peripheral blood, about 1,300 cells per microliter in the peripheral blood, about 1,400 cells per microliter in the peripheral blood, and about 1,500 cells per microliter in the peripheral blood. In some embodiments, the condition is hypereosinophilic syndrome, which can be characterized by levels of eosinophils above or about 1,000 cells per microliter in the peripheral blood. In some embodiments, the condition is hypereosinophilic syndrome, which can be characterized by levels of eosinophils above or about 1,500 cells per microliter in the peripheral blood.

In some embodiments, a subject with normal levels of basophils is a subject with levels of basophils considered to be within the normal range or limits for the particular subject and/or condition. In some embodiments, a subject with normal levels of basophils is characterized by levels of basophils of less than about 100 cells per microliter in the peripheral blood. In some embodiments, a subject with elevated levels of basophils is a subject with levels of basophils considered to be outside of the normal range or limit for the particular subject and/or condition. In some embodiments, a condition characterized by elevated levels of basophils is characterized by levels of basophils selected from above about 100 cells per microliter in the peripheral blood, above about 200 cells per microliter in the peripheral blood, above about 250 cells per microliter in the peripheral blood, above about 300 cells per microliter in the peripheral blood, above about 400 cells per microliter in the peripheral blood, and above about 500 cells per microliter in the peripheral blood.

In some embodiments, the condition is selected from a cardiovascular disease, a gastrointestinal disease, a fibrotic disease, a cancer, an endocrine disease, an ear, nose, throat or eye disease, a respiratory disease, a pulmonary disease, a skin disease, a connective tissue disease, a renal disease, a drug-induced eosinophilia, an infection-induced disease and a combination thereof.

In some embodiments, the condition is a cardiovascular disease. In some embodiments, the cardiovascular condition is Behçet disease, incomplete Kawasaki disease (iKd), eosinophil endomyocardial disease (Loeffler endocarditis), coronary restenosis, cholesterol crystal embolism, or atherosclerosis.

In some embodiments, the condition is a gastrointestinal disease. In some embodiments, the gastrointestinal disease is sclerosing cholangitis, irritable bowel disease, ulcerative colitis, sclerosing cholangitis, eosinophilic esophagitis, eosinophilic gastroenteritis, inflammatory bowel diseases, eosinophilic colitis, gluten sensitivity, or Cronkhite-Canada syndrome.

In some embodiments, the condition is a connective tissue disease. In some embodiments, the connective tissue disease is systemic sclerosis, polymyositis, dermatomyositis, systemic lupus erythematosus, or rheumatoid arthritis. In some embodiments, the connective tissue disease is Shulman's syndrome (eosinophilic fasciitis), retroperitoneal fibrosis, eosinophilia myalgia syndrome, or eosinophilic polymyositis. In some embodiments, the connective tissue disease is chronic granulomatous disease, Wegener's vasculitis and ANCA-associated vasculitis.

In some embodiments the condition is a cancer. In some embodiments, the cancer is angioimmunoblastic T-cell lymphoma, Sezary syndrome (cutaneous T-cell lymphoma), mantle cell lymphoma, Hodgkin lymphoma, non-Hodgkin lymphoma, adult T-cell leukemia/lymphoma, B-cell lymphoblastic leukemia, acute myeloid leukemia, acute promyelocytic leukemia, acute eosinophilic leukemia, acute basophilic leukemia, acute basophilic granulocytic leukemia, acute monocytic leukemia, acute lymphocytic leukemia, chronic myeloid leukemia, chronic promyelocytic leukemia, chronic eosinophilic leukemia, chronic basophilic leukemia, basophilic chronic granulocytic leukemia with hyperhistaminaemia, chronic basophilic granulocytic leukemia, chronic monocytic leukemia or large cell lymphoma.

In some embodiments, the condition is eosinophilic dermatosis associated with a hematological malignancy such as but not limited to mantle cell lymphoma, Hodgkin lymphoma, non-Hodgkin lymphoma, adult T-cell leukemia/lymphoma, B-cell lymphoblastic leukemia, acute myeloid leukemia, acute promyelocytic leukemia, acute eosinophilic leukemia, acute basophilic leukemia, acute basophilic granulocytic leukemia, acute monocytic leukemia, acute lymphocytic leukemia, chronic myeloid leukemia, chronic promyelocytic leukemia, chronic eosinophilic leukemia, chronic basophilic leukemia, basophilic chronic granulocytic leukemia with hyperhistaminaemia, chronic basophilic granulocytic leukemia, chronic monocytic leukemia, large cell lymphoma, myelofibrosis or chronic lymphocytic leukemia.

In some embodiments, the condition is a myeloproliferative disease. In some embodiments, the myeloproliferative disease is aggressive systemic mastocytosis, hypereosinophilic syndrome, eosinophilic granuloma (histiocytosis X), myelofibrosis, essential thrombocythemia or polycythemia vera.

In some embodiments, the condition is an endocrine disease. In some embodiments, the endocrine disease is eosinophilic prostatitis, Ridel's fibrous thyroiditis, or Hashimoto's thyroiditis.

In some embodiments, the condition is an ear, nose, throat or eye disease. In some embodiments, the ear, nose, throat or eye disease is non-allergic rhinitis, chronic sinusitis with nasal polyposis or polyps, nasal polyposis, hyper-IgE syndrome, eosinophilic otitis media, vernal keratoconjunctivitis, herpes stromal keratitis, Graves' ophthalmology, orbital pseudotumor, Kimura's disease, tonsillitis or cervical adenitis.

In some embodiments, the condition is a respiratory disease. In some embodiments, the respiratory disease is seasonal allergy, cypress allergy, or eosinophilic angiocentric fibrosis. In some embodiments, the respiratory disease is Churg-Strauss syndrome In some embodiments, the respiratory disease is asthma. In some embodiments, the respiratory disease is eosinophilic asthma. In some embodiments, asthma is selected from atopic asthma, allergic asthma, persistent asthma, mild asthma, moderate asthma, severe asthma, alternia-enhanced asthma and combinations thereof. In some embodiments, the respiratory disease is chronic obstructive pulmonary disease. In some embodiments, the chronic obstructive pulmonary disease is emphysema or chronic bronchitis. In some embodiments, the respiratory disease is acute bronchitis, eosinophilic bronchitis or bronchiectasis. In some embodiments, the respiratory disease is interstitial lung disease, sarcoidosis, idiopathic pulmonary fibrosis, Hamman-Rich syndrome, or antisynthetase syndrome. In some embodiments, the respiratory disease is pleural eosinophilia, bronchopulmonary aspergillosis, non-allergic rhinitis with eosinophilia syndrome, chronic eosinophilic pneumonia.

In some embodiments, the condition is a skin disease. In some embodiments, the skin disease is atopic dermatitis, chronic idiopathic urticaria, Wells' syndrome (eosinophilic cellulitis), eosinophilic pustular folliculitis, Henoch-Schönlein purpura (anaphylactoid purpura), epitheloid hemangioma, bullous pemphigoid, angiolymphoid hyperplasia with eosinophilia, eosinophilic panniculitis, angioedema with eosinophilia, Gleich's syndrome, or Omenn syndrome.

In some embodiments the condition is a urogenital disease. In some embodiments, the urogenital disease is eosinophiluria, eosinophilic prostatitis or nephrogenic systemic fibrosis.

In some embodiments, the condition is Langerhans cell histocystosis, Erdheim-Chester disease, periodontal disease, eosinophil endomyocardial disease (Loeffler endocarditis) or a drug-induced eosinophilia.

In some embodiments, the condition is drug-induced eosinophilia. In some embodiments, the drug-induced eosinophilia is drug rash with eosinophilia and systemic symptoms (DRESS), eosinophilic probiotic reaction, eosinophilia-myalgia syndrome, minocycline-induced eosinophilic pneumonia, or telaprevir-based triple therapy for chronic hepatitis associated hypereosinophilia. In some embodiments, the condition is DRESS resulting from the use of ipilimumab, or granulomatous inflammation of the central nervous system resulting from the use of ipilimumab. In some embodiments, the condition is DRESS resulting from the use of atorvastatin, ceftazidime, carbamazepine, telaprevir, or allopurinol.

In some embodiments, the condition is an infection-induced disease. In some embodiments, the condition is a tropical infection-induced disease. In some embodiments, the infection-induced disease is onchocerciasis (river blindness), eosinophilic meningitis, tropical sprue, paracoccidioidomycosis, cerebellar malaria or cerebral malaria.

In some embodiments, the condition is selected from eosinophil endomyocardial disease (Loeffler endocarditis), coronary restenosis, cholesterol crystal embolism, atherosclerosis, sclerosing cholangitis, irritable bowel disease, ulcerative colitis, eosinophilic colitis, gluten sensitivity, Cronkhite-Canada syndrome, Shulman's syndrome (eosinophilic faciitis), retroperitoneal fibrosis, nephrogenic systemic fibrosis, eosinophilic angiocentric fibrosis, angioimmunoblastic T-cell lymphoma, Sezary syndrome (cutaneous T-cell lymphoma), eosinophilic dermatosis associated with a hematological malignancy, myelodysplastic syndrome, eosinophiluria, pleural eosinophilia, eosinophilic panniculitis, angioedema with eosinophilia, Kimura's disease, bronchopulmonary aspergillosis, eosinophilic prostatitis, Ridel's fibrous thyroiditis, Hashimoto's thyroiditis, chronic sinusitis with nasal polyposis or polyps, eosinophilic otitis media, vernal keratoconjunctivitis, orbital pseudotumor, seasonal allergies, a cypress allergy, alternaria-enhanced asthma, atopic dermatitis, chronic idiopathic urticaria, Wells' syndrome (eosinophilic cellulitis), eosinophilic pustular folliculitis, Henoch-Schönlein purpura (anaphylactoid purpura), epitheloid hemangioma, bullous pemphigoig, angiolymphoid hyperplasia with eosinophilia, reno disease, Langerhans cell histocystosis, Erdheim-Chester disease, periodontal disease, drug rash with eosinophilia and systemic symptoms (DRESS), eosinophilic probiotic reaction, eosinophilia-myalgia syndrome, minocycline-induced eosinophilic pneumonia, telaprevir-based triple therapy for chronic hepatitis associated hypereosinophilia, DRESS resulting from the use of ipilimumab, granulomatous inflammation of the central nervous system resulting from the use of ipilimumab, DRESS resulting from the use of atorvastatin, ceftazidime, carbamazepine, telaprevir, or allopurinol, onchocerciasis (river blindness), eosinophilic meningitis, tropical sprue, paracoccidioidomycosis, malaria, cerebral malaria, cerebellar malaria, incomplete Kawasaki disease (iKd), Behçet disease, tonsolitis and cervical adenitis, Graves' ophthalmology, Churg-Strauss syndrome, nasal polyposis, eosinophilic esophagitis, hypereosinophilic syndrome, chronic granulomatous disease, Wegener's vasculitis and ANCA-associated vasculitis, asthma, allergic rhinitis, non-allergic rhinitis, non-allergic rhinitis with eosinophilia syndrome, eosinophilic granuloma (histiocytosis X), eosinophilic polymyositis, chronic eosinophilic pneumonia, eosinophilic gastroenteritis, aggressive systemic mastocytosis, Gleich's syndrome, eosinophilia myalgia syndrome, Omenn syndrome, hyper-IgE syndrome, eosinophilic leukemia, inflammatory bowel diseases, herpes stromal keratitis, and any combination thereof.

In some embodiments, the condition is selected from eosinophil endomyocardial disease (Loeffler endocarditis), cholesterol crystal embolism, sclerosing cholangitis, irritable bowel disease, ulcerative colitis, eosinophilic colitis, gluten sensitivity, Cronkhite-Canada syndrome, Shulman's syndrome (eosinophilic faciitis), retroperitoneal fibrosis, nephrogenic systemic fibrosis, eosinophilic angiocentric fibrosis, angioimmunoblastic T-cell lymphoma, Sezary syndrome (cutaneous T-cell lymphoma), eosinophilic dermatosis associated with a hematological malignancy, myelodysplastic syndrome, eosinophiluria, pleural eosinophilia, eosinophilic panniculitis, angioedema with eosinophilia, Kimura's disease, bronchopulmonary aspergillosis, eosinophilic prostatitis, Ridel's fibrous thyroiditis, Hashimoto's thyroiditis, chronic sinusitis with nasal polyposis or polyps, eosinophilic otitis media, vernal keratoconjunctivitis, orbital pseudotumor, seasonal allergies, a cypress allergy, alternaria-enhanced asthma, atopic dermatitis, chronic idiopathic urticaria, Wells' syndrome (eosinophilic cellulitis), eosinophilic pustular folliculitis, Henoch-Schönlein purpura (anaphylactoid purpura), epitheloid hemangioma, bullous pemphigoig, angiolymphoid hyperplasia with eosinophilia, reno disease, Langerhans cell histocystosis, Erdheim-Chester disease, periodontal disease, drug rash with eosinophilia and systemic symptoms (DRESS), eosinophilic probiotic reaction, eosinophilia-myalgia syndrome, minocycline-induced eosinophilic pneumonia, telaprevir-based triple therapy for chronic hepatitis associated hypereosinophilia, DRESS resulting from the use of ipilimumab, granulomatous inflammation of the central nervous system resulting from the use of ipilimumab, DRESS resulting from the use of atorvastatin, ceftazidime, carbamazepine, telaprevir, or allopurinol, onchocerciasis (river blindness), eosinophilic meningitis, tropical sprue, paracoccidioidomycosis, malaria, cerebral malaria, cerebellar malaria, incomplete Kawasaki disease (iKd), Behçet disease, tonsolitis and cervical adenitis, Graves' ophthalmology, Churg-Strauss syndrome, nasal polyposis, eosinophilic esophagitis, hypereosinophilic syndrome, chronic granulomatous disease, Wegener's vasculitis and ANCA-associated vasculitis, asthma, allergic rhinitis, non-allergic rhinitis, non-allergic rhinitis with eosinophilia syndrome, eosinophilic granuloma (histiocytosis X), eosinophilic polymyositis, chronic eosinophilic pneumonia, eosinophilic gastroenteritis, aggressive systemic mastocytosis, Gleich's syndrome, eosinophilia myalgia syndrome, Omenn syndrome, hyper-IgE syndrome, eosinophilic leukemia, inflammatory bowel diseases, herpes stromal keratitis, and any combination thereof.

In some embodiments, the condition is characterized by eosinophils or elevated eosinophil levels. In some embodiments, the condition is selected from the group consisting of incomplete Kawasaki disease (iKd), Behçet disease, tonsolitis and cervical adenitis, Graves' ophthalmology, Churg-Strauss syndrome, nasal polyposis, atopic dermatitis, eosinophilic esophagitis, hypereosinophilic syndrome, asthma, allergic rhinitis, non-allergic rhinitis with eosinophilia syndrome, eosinophilic granuloma (histiocytosis X), eosinophilic polymyositis, chronic eosinophilic pneumonia, eosinophilic gastroenteritis, aggressive systemic mastocytosis, Gleich's syndrome, eosinophilia myalgia syndrome, Omenn syndrome, hyper-IgE syndrome, eosinophilic leukemia, and inflammatory bowel diseases.

In some embodiments, the condition is characterized by basophils or elevated basophil levels. In some embodiments, the condition is herpes stromal keratitis.

In some embodiments, the condition is aggressive systemic mastocytosis.

In some embodiments, the condition is angioimmunoblastic T-cell lymphoma, Sezary syndrome (cutaneous T-cell lymphoma), mantle cell lymphoma, Hodgkin lymphoma, non-Hodgkin lymphoma, adult T-cell leukemia/lymphoma, B-cell lymphoblastic leukemia, acute myeloid leukemia, acute promyelocytic leukemia, acute eosinophilic leukemia, acute basophilic leukemia, acute basophilic granulocytic leukemia, acute monocytic leukemia, acute lymphocytic leukemia, chronic myeloid leukemia, chronic promyelocytic leukemia, chronic eosinophilic leukemia, chronic basophilic leukemia, basophilic chronic granulocytic leukemia with hyperhistaminaemia, chronic basophilic granulocytic leukemia, chronic monocytic leukemia, large cell lymphoma, myelofibrosis or polycythemia vera.

In some embodiments, the eosinophilic dermatosis associated with a hematological malignancy is associated with mantle cell lymphoma, Hodgkin lymphoma, non-Hodgkin lymphoma, adult T-cell leukemia/lymphoma, B-cell lymphoblastic leukemia, acute myeloid leukemia, acute promyelocytic leukemia, acute eosinophilic leukemia, acute basophilic leukemia, acute basophilic granulocytic leukemia, acute monocytic leukemia, acute lymphocytic leukemia, chronic myeloid leukemia, chronic promyelocytic leukemia, chronic eosinophilic leukemia, chronic basophilic leukemia, basophilic chronic granulocytic leukemia with hyperhistaminaemia, chronic basophilic granulocytic leukemia, chronic monocytic leukemia, large cell lymphoma, myelofibrosis, chronic lymphocytic leukemia or a combination thereof.

In some embodiments, the condition is hypereosinophilic syndrome.

In some embodiments, the condition is chronic sinusitis with nasal polyps.

In some embodiments, the condition is asthma. In some embodiments, the condition is eosinophilic asthma. In some embodiments, asthma is selected from atopic asthma, allergic asthma, persistent asthma, mild asthma, moderate asthma, severe asthma and any combination thereof.

In some embodiments, the condition is a secondary response to an infection-induced disease. In some embodiments, the condition is a secondary response to a tropical infection-induced disease. In some embodiments, the infection-induced disease is onchocerciasis (river blindness), eosinophilic meningitis, tropical sprue, paracoccidioidomycosis, malaria, cerebellar malaria or cerebral malaria.

In another embodiment, the condition may include systemic inflammation. Systemic inflammation is not confined to a particular tissue, may overwhelm the body, and may involve the endothelium and other organ systems. When it is due to infection, the term sepsis may be applied, with the terms bacteremia being applied specifically as provoking bacterial sepsis and viremia specifically as provoking viral sepsis. Vasodilation and organ dysfunction are serious problems associated with sepsis that may lead to septic shock and death.

In another embodiment, the condition may be arthritis. Arthritis includes a group of conditions involving damage to the joints of the body often involving the inflammation of the synovium including, without limitation, osteoarthritis, rheumatoid arthritis, juvenile idiopathic arthritis, spondyloarthropathies such as ankylosing spondylitis, reactive arthritis (Reiter's syndrome), psoriatic arthritis, enteropathic arthritis associated with inflammatory bowel disease, Whipple disease and Behçet disease, septic arthritis, gout (also known as gouty arthritis, crystal synovitis, metabolic arthritis), pseudogout (calcium pyrophosphate deposition disease), and Still's disease. Arthritis can affect a single joint (monoarthritis), two to four joints (oligoarthritis) or five or more joints (polyarthritis) and can be either an auto-immune disease or a non-autoimmune disease.

In some embodiments, the condition, disease or disorder is not a neurodegenerative disease. In some embodiments, the condition is not Parkinson's disease, Alzheimer's disease or amyotrophic lateral sclerosis.

In some embodiments, the condition is a veterinary disease. In some embodiments, a veterinary disease is a disease that occurs in non-human animals.

In some embodiments, the veterinary disease is a skin disease. In some embodiments, the skin disease is eosinophilic dermatosis, eosinophilic granuloma complex, or mosquito bite hypersensitivity. In some embodiments, subtypes of eosinophilic granuloma complex include but are not limited to eosinophilic plaque, eosinophilic granuloma, and eosinophilic ulcers. In some embodiments, the eosinophilic granuloma complex is equine eosinophilic granuloma in horses or feline miliary dermatitis in cats. In some embodiments, the skin disease is feline herpesvirus dermatitis and stomatosis, canine facial eosinophilic folliculitis and furunculosis, canine atopic dermatitis, canine eosinophilic dermatitis with edema (Wells' syndrome), or canine allergic dermatitis.

In some embodiments, the veterinary disease is a gastrointestinal disease. In some embodiments, the gastrointestinal disease is eosinophilic gastroenteritis, feline intestinal eosinophilic sclerosing fibroplasia, or masticatory muscle myositis.

In some embodiments, the veterinary disease is a respiratory disease. In some embodiments, the respiratory disease is feline bronchial asthma, eosinophilic bronchopneumopathy, or nasal mycotic granuloma.

In some embodiments, the veterinary disease is a systemic disease. In some embodiments, the systemic disease is multisystemic eosinophilic epitheliotrophic disease (MEED), eosinophilic leukemia, eosinophilic myositis, equine nodular disease, or eosinophilic keratitis.

Various embodiments are directed to a method of treating a condition characterized by pathogenic basophils, eosinophils and/or neutrophils in a patient comprising administering to the patient a therapeutically effective amount of (6R)-2-amino-4,5,6,7-tetrahydro-6-(propylamino)benzothiazole, or a pharmaceutically acceptable salt thereof. In some embodiments, the condition is characterized by increased levels of basophils, eosinophils and/or neutrophils.

Various embodiments are directed to a method of treating a condition characterized by pathogenic basophils, eosinophils or neutrophils in a patient comprising administering to the patient a pharmaceutical composition comprising a therapeutically effective amount of (6R)-2-amino-4,5,6,7-tetrahydro-6-(propylamino)benzothiazole, or a pharmaceutically acceptable salt thereof. In some embodiments, the condition is characterized by increased levels of basophils, eosinophils and/or neutrophils.

In some embodiments, the condition is an allergic condition. In still other embodiments, the condition is an inflammatory condition. In some embodiments, the condition is selected from the group consisting of Incomplete Kawasaki disease (iKd), Behçet Disease, tonsolitis and cervical adenitis, Graves' ophthalmology, chronic eosinophilic pneumonia, eosinophilic gastroenteritis, aggressive systemic mastocytosis, Gleich's syndrome, eosinophilia myalgia syndrome, Omenn syndrome, hyper-IgE syndrome, Churg Strauss syndrome, nasal polyposis, atopic dermatitis, eosinophilic esophagitis, hypereosinophilic syndrome, allergic rhinitis, non-allergic rhinitis with eosinophilia syndrome, eosinophilic granuloma (histiocytosis X), eosinophilic polymyositis, allergy, drug induced injuries, cutaneous reactions and disorders including bullous pemphigoid, chronic granulomatous disease, vasculitides including Wegener's and ANCA-associated vasculitis, intracerebral hemorrhage, spinal cord injury, traumatic brain injury, multiple sclerosis and other neuroinflammatory diseases, neuromyelitis optica, herpes stromal keratitis, immune-mediated neurologic disorders, microglia-derived inflammation, inflammatory bowel disease, respiratory disorders including asthma and COPD, autoimmune disorders including insulin dependent diabetes mellitus, systemic lupus erythematosus and rheumatoid arthritis, non-insulin dependent diabetes, dermatitis herpetiformis, parasitic infections, malaria-induced cerebellar damage, Hodgkin's lymphoma, Non-Hodgkin lymphoma, systemic autoimmune diseases, cholesterol embolism, coccidioidomycosis, ovarian cancer, and neurodegenerative disease. In some embodiments, the condition is selected from the group consisting of Incomplete Kawasaki disease (iKd), Behçet Disease, tonsolitis and cervical adenitis, Graves' ophthalmology, chronic eosinophilic pneumonia, eosinophilic gastroenteritis, aggressive systemic mastocytosis, Gleich's syndrome, eosinophilia myalgia syndrome, Omenn syndrome, hyper-IgE syndrome, Churg Strauss syndrome, nasal polyposis, eosinophilic esophagitis, hypereosinophilic syndrome, allergic rhinitis, non-allergic rhinitis with eosinophilia syndrome, eosinophilic granuloma (histiocytosis X), eosinophilic polymyositis, allergy, drug induced injuries, cutaneous reactions and disorders including bullous pemphigoid, chronic granulomatous disease, vasculitides including Wegener's and ANCA-associated vasculitis, spinal cord injury, multiple sclerosis and other neuroinflammatory diseases, neuromyelitis optica, herpes stromal keratitis, immune-mediated neurologic disorders, microglia-derived inflammation, inflammatory bowel disease, respiratory disorders including asthma and COPD, autoimmune disorders including insulin dependent diabetes mellitus, systemic lupus erythematosus and rheumatoid arthritis, dermatitis herpetiformis, parasitic infections, malaria-induced cerebellar damage, Hodgkin's lymphoma, Non-Hodgkin lymphoma, systemic autoimmune diseases, cholesterol embolism, coccidioidomycosis, and ovarian cancer.

In some embodiments, the condition is characterized by pathogenic eosinophils or elevated eosinophil levels. In some embodiments, the condition is selected from the group consisting of incomplete Kawasaki disease (iKd), Behçet Disease, tonsolitis and cervical adenitis, Graves' ophthalmology, Churg Strauss, nasal polyposis, atopic dermatitis, eosinophilic esophagitis, hypereosinophilic syndrome, asthma, allergic rhinitis, non-allergic rhinitis with eosinophilia syndrome, eosinophilic granuloma (histiocytosis X), eosinophilic polymyositis, chronic eosinophilic pneumonia, eosinophilic gastroenteritis, aggressive systemic mastocytosis, Gleich's syndrome, eosinophilia myalgia syndrome, Omenn syndrome, hyper-IgE syndrome, as eosinophilic leukemia, and inflammatory bowel diseases.

In some embodiments, the condition is characterized by pathogenic basophils or elevated basophil levels. In some embodiments, the condition is selected from the group consisting of allergy, and herpes stromal keratitis.

In some embodiments, the condition is characterized by pathogenic neutrophils or elevated neutrophil levels. In some embodiments, the condition is selected from the group consisting of drug induced injuries, cutaneous reactions and disorders including bullous pemphigoid, chronic granulomatous disease, vasculitides including Wegener's and ANCA-associated vasculitis, intracerebral hemorrhage, spinal cord injury, traumatic brain injury, multiple sclerosis, neuromyelitis optica, immune-mediated neurologic disorders, inflammatory bowel disease, respiratory disorders including asthma and COPD, autoimmune disorders including IDDM and SLE and rheumatoid arthritis, non-insulin dependent diabetes, herpes stromal keratitis and neurodegenerative diseases. In some embodiments, the condition is selected from the group consisting of drug induced injuries, cutaneous reactions and disorders including bullous pemphigoid, chronic granulomatous disease, vasculitides including Wegener's and ANCA-associated vasculitis, spinal cord injury, multiple sclerosis, neuromyelitis optica, immune-mediated neurologic disorders, inflammatory bowel disease, respiratory disorders including asthma and COPD, autoimmune disorders including IDDM and SLE and rheumatoid arthritis and herpes stromal keratitis.

In some embodiments, the condition is not a neurodegenerative disease. In some embodiments, the condition is not Parkinson's disease, Alzheimer's disease or amyotrophic lateral sclerosis.

In some embodiments, administering a therapeutically effective amount of dexpramipexole or a pharmaceutically acceptable salt thereof may include administering daily doses of about 0.1 mg or more, about 1 mg or more, about 10 mg or more, about 50 mg or more, about 75 mg or more, about 100 mg or more, about 125 mg or more, about 150 mg or more, about 175 mg or more, about 200 mg or more, about 225 mg or more, about 250 mg or more, about 275 mg or more, about 300 mg or more, about 400 mg or more, about 450 mg or more, about 500 mg or more, about 600 mg or more, about 700 mg or more, about 800 mg or more or about 1,000 mg or more, about 1,200 mg or more or about 1,500 mg or more.

In some embodiments, the therapeutically effective amount of dexpramipexole or a pharmaceutically acceptable salt thereof is from about 50 mg to about 1,500 mg per day. In some embodiments, the therapeutically effective amount is from about 100 mg to about 1,500 mg per day. In some embodiments, the therapeutically effective amount is from about 150 mg to about 1,500 mg per day. In some embodiments, the therapeutically effective amount is from about 300 mg to about 1,500 mg per day. In some embodiments, the therapeutically effective amount is from about 50 mg to about 300 mg per day. In some embodiments, the therapeutically effective amount is from about 150 mg to about 300 mg per day.

In some embodiments, administering a therapeutically effective amount comprises administering the daily dose as a fraction of the daily dose (as described herein) two or more times per day. In some embodiments, administering a therapeutically effective amount comprises administering a dose equal to about half of a daily dose twice per day. In some embodiments, the dose is administered every about 12 hours. In some embodiments, administering a therapeutically effective amount comprises administering about 75 mg two times per day. In some embodiments, administering a therapeutically effective amount comprises administering about 25 mg two times per day, about 75 mg two times per day, about 150 mg two times per day, or about 300 mg two times per day.

In some embodiments, administering a therapeutically effective amount comprises administering a single unit dose of dexpramipexole of about 0.1 mg or more, about 1 mg or more, about 10 mg or more, about 25 mg or more, about 50 mg or more, about 75 mg or more, about 100 mg or more, about 125 mg or more, about 150 mg or more, about 175 mg or more, about 200 mg or more, about 225 mg or more, about 250 mg or more, about 275 mg or more, about 300 mg or more, about 400 mg or more, about 450 mg or more, about 500 mg or more, about 600 mg or more, about 700 mg or more, about 800 mg or more, about 1,000 mg or more, about 3,000 mg or more, or about 5,000 mg or more. In some embodiments, the single unit dose comprises from about 600 mg to about 900 mg of dexpramipexole.

In some embodiments, administering a therapeutically effective amount comprises administering a single unit dose amount of dexpramipexole or a pharmaceutically acceptable salt thereof from about 25 mg to about 5,000 mg, from about 50 mg to about 5,000 mg, from about 100 mg to about 5,000 mg, from about 150 mg to about 5,000 mg, from about 200 mg to about 5,000 mg, from about 250 mg to about 5,000 mg, from about 300 mg to about 5,000 mg, from about 400 mg to about 5,000 mg, from 450 mg to about 5,000 mg, from about 100 mg to about 3,000 mg, from about 150 mg to about 3,000 mg, from about 200 mg to about 3,000 mg, from about 250 mg to about 3,000 mg, from about 300 mg to about 3,000 mg, from about 400 mg to about 3,000 mg, from 450 mg to about 3,000 mg, from about 100 mg to about 1,000 mg, from about 150 mg to about 1,000 mg, from about 200 mg to about 1,000 mg, from about 250 mg to about 1,000 mg, from about 300 mg to about 1,000 mg, from about 400 mg to about 1,000 mg, from 450 mg to about 1,000 mg, from about 500 mg to about 1000 mg, from about 600 mg to about 1,000 mg. In some embodiments, the single unit dose amount may be 10 mg/day to 1,500 mg/day, more preferably 100 mg/day to 600 mg/day. In some embodiments, the single unit dose amount of dexpramipexole or a pharmaceutically acceptable salt thereof is from about 600 mg to about 900 mg. In some embodiments, the single unit dose amount of dexpramipexole or a pharmaceutically acceptable salt thereof is from about 300 mg to about 1,500 mg. In some embodiments, such single unit doses may be administered once per day or multiple times per day, such as twice per day or three times per day.

In another embodiment, administering a therapeutically effective amount comprises administering a single unit dose comprising at least about 50 mg of dexpramipexole or a pharmaceutically acceptable salt thereof and no more than about 1.5 mg of (S)-pramipexole. In another aspect, the present invention provides a single unit dose comprising at least about 75 mg of dexpramipexole or a pharmaceutically acceptable salt thereof and no more than about 1.5 mg of (S)-pramipexole, or at least about 100 mg of dexpramipexole or a pharmaceutically acceptable salt thereof and no more than about 1.5 mg of (S)-pramipexole. In some embodiments, the single unit dose comprises no more than 1.0 mg, no more than 0.333 mg no more than 0.3 mg no more than 0.2 mg, no more than 0.125 mg of (S)-pramipexole.

In some embodiments, the single unit dose further comprises a pharmaceutically acceptable carrier. In some embodiments, such single unit doses may be administered once per day or multiple times per day, such as twice per day or three times per day.

One of ordinary skill in the art will understand and appreciate the dosages and timing of the dosages to be administered to a subject in need thereof. The doses and duration of treatment may vary, and may be based on assessment by one of ordinary skill in the art based on monitoring and measuring improvements in neuronal and non-neuronal tissues. This assessment may be made based on outward physical signs of improvement, such as increased muscle control, or on internal physiological signs or markers. The doses may also depend on the condition or disease being treated, the degree of the condition or disease being treated and further on the age, weight, body mass index and body surface area of the subject.

In some embodiments, therapeutically effective amounts, daily doses, or single unit doses of dexpramipexole may be administered once per day or multiple times per day, such as 1 to 5 doses, twice per day or three times per day.

Embodiments are also directed to a dosage regimen for administering dexpramipexole or a pharmaceutically acceptable salt thereof to treat the conditions disclosed herein. For example, in some embodiments, the methods described herein may comprise a dosage regimen that may include a plurality of daily doses having an equal amount of dexpramipexole or a pharmaceutically acceptable salt thereof as the initial dose in one or more unit doses. In other embodiments, the dosage regimen may include an initial dose of dexpramipexole or a pharmaceutically acceptable salt thereof in one or more unit doses, then a plurality of daily doses having a lower amount of dexpramipexole or a pharmaceutically acceptable salt thereof as the initial dose in one or more unit doses. The dosage regimen may administer an initial dose followed by one or more maintenance doses. The plurality of doses following the administering of an initial dose may be maintenance doses.

Such embodiments are not limited by the amount of the initial dose and daily doses. For example, in particular embodiments, the initial dose and each of the plurality of daily doses may be from about 0.1 mg or more, about 1 mg or more, about 10 mg or more, about 50 mg or more, about 75 mg or more, about 100 mg or more, about 125 mg or more, about 150 mg or more, about 175 mg or more, about 200 mg or more, about 225 mg or more, about 250 mg or more, about 275 mg or more, about 300 mg or more, about 400 mg or more, about 450 mg or more, about 500 mg or more, about 600 mg or more, about 700 mg or more, about 800 mg or more, about 1,000 mg or more, 1,200 mg or more, or about 1,500 mg or more of dexpramipexole. In some embodiments, the one or more unit doses of the dosage regimen may be 1 to 5 unit doses, and in such embodiments, each of the one or more unit doses may be substantially equal.

In some embodiments, two unit doses of about 75 mg are administered daily, wherein each unit dose may be substantially equal. In some embodiments, three unit doses of about 75 mg are administered daily, wherein each unit dose may be substantially equal.

In other embodiments, the maintenance therapy dosing may include administering less than the initial daily dose, such as less than about 50 mg, less than about 75 mg, less than about 150 mg, less than about 300 mg, or less than 600 mg of dexpramipexole per day. Following the initial dosing regimen, the subject may be administered a maintenance dosing regimen of, for example, about 0.1 mg or more, about 1 mg or more, about 10 mg or more, about 50 mg or more, about 75 mg or more, about 100 mg or more, about 125 mg or more, about 150 mg or more, about 175 mg or more, about 200 mg or more, about 225 mg or more, about 250 mg or more, about 275 mg or more, about 300 mg or more, about 400 mg or more, about 450 mg or more, about 500 mg or more, about 600 mg or more, about 700 mg or more, about 800 mg or more, or about 1,000 mg or more, about 1,200 mg or more, or about 1,500 mg or more of dexpramipexole for a period of time such as, for example, at least 12 weeks or more or at least 6 months or 1, 2, 3, 5 or 10 years or more.

In further embodiments, the method may include an initial dosing regimen and a maintenance dosing regimen. In certain embodiments, the initial dosing regimen may include administering a higher dose of dexpramipexole or a pharmaceutically acceptable salt thereof than the maintenance dosing regimen as either a single administration or by administering an increased dosage for a limited period of time prior to beginning a maintenance dosing regimen of dexpramipexole or a pharmaceutically acceptable salt thereof. In some embodiments, subjects undergoing a maintenance regimen may be administered one or more higher-dosage treatments at one or more times during the maintenance dosage regimen.

In certain embodiments, the initial dosing regimen and the maintenance dosing regimen may be about 50 mg to about 1500 mg or more of dexpramipexole, about 150 mg to about 300 mg or more of dexpramipexole, about 300 mg to about 500 mg or more of dexpramipexole per day, or from about 300 mg to about 600 mg or more of dexpramipexole per day.

In some embodiments, the initial dosing regimen and the maintenance dosing regimen may include administering dexpramipexole or a pharmaceutically acceptable salt thereof once per day, multiple times per day, such as twice per day or three times per day. In such embodiments, the dosage regimen may continue administering an initial dose for 1, 2, 3, 4, 5, 6 or 7 days, up to 4 weeks, up to 8 weeks or up to 12 weeks. In some embodiments, the dosage regimen for administering an initial dose and/or a maintenance dose may continue for an extended period of time. Various embodiments are directed to a dosing regimen for dexpramipexole or a pharmaceutically acceptable salt thereof in which maintenance doses are maintained for an extended period of time without titration or otherwise changing the dosing regimen. In such embodiments, the extended period of time may be about 12 weeks or longer, about 6 months or longer, about 1 year or longer, 2, 3, 4, 5, or 10 years or longer, and in certain embodiments, an indefinite period of time.

Each of the dosage regimens for dexpramipexole described herein may be used in any of the methods, and the dosing regimen may be carried out using any of the compositions described herein.

In some embodiments, treatment with a therapeutically effective amount of dexpramipexole is without the adverse side effects associated with dopamine agonism.

Some embodiments further comprise administering to the subject a therapeutically effective amount of one or more secondary agents. In some embodiments, the therapeutically effective amount of dexpramipexole or salt thereof and the therapeutically effective amount of the one or more secondary agents may be administered individually or combined into a single dosage composition. In some embodiments, the therapeutically effective amount of dexpramipexole or salt thereof and the therapeutically effective amount of the one or more secondary agents are administered simultaneously or sequentially.

In some embodiments, the one or more secondary agent is any drug that induces anti-inflammatory effects or is capable of decreasing levels of eosinophils and/or basophils in the subject. In some embodiments, the secondary agent is an antibody. In some embodiments, the secondary agent is not dexpramipexole. In some embodiments, the secondary agent is selected from a corticosteroid, a non-steroidal anti-inflammatory drug (NSAID), a tyrosine kinase inhibitor, a fusion protein, a monoclonal antibody directed against one or more pro-inflammatory cytokines, a chemotherapeutic agent and a combination thereof. In some embodiments, the secondary agent may be a glucocorticoid, a corticosteroid, a non-steroidal anti-inflammatory drug (NSAID), a phenolic antioxidant, an anti-proliferative drug, a tyrosine kinase inhibitor, an anti IL-5 or an IL5 receptor monoclonal antibody, an anti IL-13 or an anti IL-13 receptor monoclonal antibody, an IL-4 or an IL-4 receptor monoclonal antibody, an anti IgE monoclonal antibody, a monoclonal antibody directed against one or more pro-inflammatory cytokines, a TNF-α inhibitor, a fusion protein, a chemotherapeutic agent or a combination thereof. In some embodiments, the secondary agent is an anti-inflammatory drug. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, curcumin, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, lysofylline, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, mepolizumab, prodrugs thereof, and a combination thereof. In some embodiments the tyrosine kinase inhibitor is imatinib. In some embodiments the anti IL-5 monoclonal antibody is mepolizumab or reslizumab. In some embodiments, the IL-5 receptor monoclonal antibody is benralizumab. In some embodiments, the anti IL-13 monoclonal antibody is lebrikizumab or dulipumab. In some embodiments the anti IL-4 monoclonal antibody is dulipumab. In some embodiments, the anti IgE monoclonal antibody is omalizumab. In some embodiments, the TNF-α inhibitor is infliximab, adalimumab, certolizumab pegol, or golimumab. In some embodiments, the fusion protein is etanercept.

Various embodiments may also comprise an induction step comprising administration of a therapeutically effective amount of a secondary agent that induces anti-inflammatory effects or is capable of decreasing levels of eosinophils and/or basophils in the subject prior to administration of a therapeutically effective amount of dexpramipexole or a pharmaceutically acceptable salt thereof. In some embodiments, administration of the secondary agent may continue or may become discontinued once administration of dexpramipexole or pharmaceutically acceptable salt thereof starts.

In some embodiments, the induction step comprises administering a therapeutically effective amount of the secondary agent for a period of about 1 day to about 6 months. In some embodiments, the secondary agent is administered for a period of about 1 day, about 2 days, about 3 days, about 4 days, about 5 days, about 6 days, about 1 week, about 2 weeks, about 3 weeks, about 1 month, about 2 months, about 3 months, about 4 months, about 5 months, or about 6 months. In some embodiments, the induction step comprises administering a therapeutically effective amount of the secondary agent for a period of less than 1 week, about 1 to 2 weeks, about 2 to 3 weeks, about 3 to 4 weeks, about 1 to 2 months, about 2 to 3 months, or about 3 to 4 months. In yet other embodiments, the induction step comprises administering a therapeutically effective amount of the secondary agent until a pre-determined level of eosinophils and/or basophils is reached, after which the induction step is discontinued, titrated out, or a combination thereof. In some embodiments, the induction step may use any of the methods described herein. In some embodiments, the induction step is followed by the administration of the dosage regimens for dexpramipexole described herein as well as any of the compositions described herein.

In any of the embodiments described, a therapeutically effective amount of dexpramipexole or a pharmaceutically acceptable salt thereof and a therapeutically effective amount of one or more of the secondary agents described above may be provided adjunctively in separate pharmaceutical compositions or in a single dose pharmaceutical composition in which the dexpramipexole or a pharmaceutically acceptable salt thereof and one or more secondary agent are combined. In some embodiments, the one or more secondary agent is a therapeutic agent capable of decreasing levels of eosinophils and/or basophils in the subject.

Specific modes of administration of dexpramipexole or salt thereof will depend on the indication. The selection of the specific route of administration and the dose regimen may be adjusted or titrated by the clinician according to methods known to the clinician in order to obtain the optimal clinical response. The amount of compound to be administered may be that amount which is therapeutically effective. The dosage to be administered may depend on the characteristics of the subject being treated, e.g., the particular animal or human subject treated, age, weight, body mass index, body surface area, health, types of concurrent treatment, if any, and frequency of treatments, and can be easily determined by one of skill in the art (e.g., by the clinician).

In the embodiments described herein, the therapeutically effective amount of dexpramipexole or pharmaceutically acceptable salt thereof may be administered in a pharmaceutical composition. Each of the pharmaceutical compositions described herein may be used in any of the methods or dosage regimens described herein.

In some embodiments, administering a therapeutically effective amount of dexpramipexole or a pharmaceutically acceptable salt thereof may include administering dexpramipexole or a pharmaceutically acceptable salt thereof in a controlled release form.

Pharmaceutical compositions containing dexpramipexole or a pharmaceutically acceptable salt thereof in a solid dosage may include, but are not limited to, softgels, tablets, capsules, cachets, pellets, pills, powders and granules; topical dosage forms which include, but are not limited to, solutions, powders, fluid emulsions, fluid suspensions, semisolids, ointments, pastes, creams, gels and jellies, and foams; and parenteral dosage forms which include, but are not limited to, solutions, suspensions, emulsions, and dry powder; comprising an effective amount of a polymer or copolymer of the present invention.

It is also known in the art that the active ingredients may be contained in such compositions with pharmaceutically acceptable diluents, fillers, disintegrants, binders, lubricants, surfactants, hydrophobic vehicles, water-soluble vehicles, emulsifiers, buffers, humectants, moisturizers, solubilizers, preservatives and the like. The means and methods for administration are known in the art and an artisan can refer to various pharmacologic references for guidance. For example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980) can be consulted.

In some embodiments, pharmaceutical compositions may be suitable for oral administration such as, for example, a solid oral dosage form or a capsule, and in certain embodiments, the composition may be a tablet. Such tablets may include any number of additional agents such as, for example, one or more binder, one or more lubricant, one or more diluent, one or more surface active agent, one or more dispersing agent, one or more colorant, and the like. Such tablets may be prepared by any method known in the art, for example, by compression or molding. Compressed tablets may be prepared by compressing in a suitable machine the ingredients of the composition in a free-flowing form such as a powder or granules, and molded tablets may be made by molding in a suitable machine a mixture of the powdered compound moistened with an inert liquid diluent. The tablets, of some embodiments, may be uncoated and, in other embodiments, they may be coated by known techniques.

In other embodiments, the pharmaceutical compositions may be provided in a dragee core with suitable coatings. In such embodiments, dragee cores may be prepared using concentrated sugar solutions, which may optionally contain gum arabic, talc, polyvinyl pyrrolidone, carbopol gel, polyethylene glycol, and/or titanium dioxide, lacquer solutions, and suitable organic solvents or solvent mixtures. In some embodiments, dyestuffs or pigments may be added to the tablets or dragee coatings for identification or to characterize different combinations of active compound doses. In yet other embodiments, pharmaceutical compositions including a therapeutically effective amount of dexpramipexole prepared for oral administration may include, but are not limited to, push-fit capsules made of gelatin, as well as soft, sealed capsules made of gelatin and a plasticizer, such as glycerol or sorbitol. The push-fit capsules may contain the active ingredients in admixture with filler such as, e.g., lactose, binders such as, e.g., starches, and/or lubricants such as, e.g., talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All compositions for oral administration should be in dosages suitable for such administration.

In embodiments in which the tablets and dragee cores are coated, the coatings may delay disintegration and absorption in the gastrointestinal tract and thereby providing a sustained action over a longer period. Additionally, such coatings may be adapted for release of dexpramipexole or a pharmaceutically acceptable salt thereof in a predetermined pattern (e.g., in order to achieve a controlled release composition) or it may be adapted not to release the active compound until after passage of the stomach (enteric coating). Suitable coatings encompassed by such embodiments may include, but are not limited to, sugar coating, film coating (e.g., hydroxypropyl methylcellulose, methylcellulose, methyl hydroxyethyl cellulose, hydroxypropyl cellulose, carboxymethylcellulose, acrylate copolymers, polyethylene glycols and/or polyvinylpyrrolidone), or an enteric coating (e.g., methacrylic acid copolymer, cellulose acetate phthalate, hydroxypropylmethylcellulose phthalate, hydroxypropyl methylcellulose acetate succinate, polyvinyl acetate phthalate, shellac, and/or ethyl cellulose). Furthermore, a time delay material such as, for example, glyceryl monostearate or glyceryl distearate may be incorporated into the coatings of some embodiments. In still other embodiments, solid tablet compositions may include a coating adapted to protect the composition from unwanted chemical changes, for example, to reduce chemical degradation prior to the release of the active drug substance.

In some embodiments, the pharmaceutical compositions including dexpramipexole or a pharmaceutically acceptable salt thereof may be prepared as suspensions, solutions or emulsions in oily or aqueous vehicles suitable for injection. In such embodiments, such liquid compositions may further include formulatory agents such as suspending, stabilizing and or dispersing agents formulated for parenteral administration. Such injectable compositions may be administered by any route, for example, subcutaneous, intravenous, intramuscular, intra-arterial or bolus injection or continuous infusion, and in embodiments in which injectable compositions are administered by continuous infusion, such infusion may be carried out for a period of about 15 minutes to about hours. In certain embodiments, compositions for injection may be presented in unit dosage form, e.g., in ampoules or in multi-dose containers, with an added preservative.

In other embodiments, dexpramipexole may be formulated as a depot preparation, and such long acting compositions may be administered by implantation (for example subcutaneously or intramuscularly) or by intramuscular injection. Depot injections may be administered at about 1 to about 6 months or longer intervals. In some embodiments, the frequency of doses of the dexpramipexole described herein administered by depot injection may be once a month, every three months, or once a year. The compounds may be formulated with suitable polymeric or hydrophobic materials (for example, as an emulsion in an acceptable oil) or ion exchange resins, or as sparingly soluble derivatives, for example, as a sparingly soluble salt.

In still other embodiments, pharmaceutical compositions including dexpramipexole or a pharmaceutically acceptable salt thereof may be formulated for buccal or sublingual administration. In such embodiments, the pharmaceutical compositions may be prepared as chewable tablets, flash melts or lozenges formulated in any conventional manner.

In yet other embodiments, pharmaceutical compositions including dexpramipexole or a pharmaceutically acceptable salt thereof may be formulated for administration by inhalation. In such embodiments, pharmaceutical compositions may be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

In further embodiments, pharmaceutical compositions including dexpramipexole or a pharmaceutically acceptable salt thereof may be administered intranasally or by inhalation including, but not limited to, an intranasal spray or by pulmonary inhalation with an appropriate carrier. One suitable route of administration is a depot form formulated from a biodegradable suitable polymer, e.g., poly-D,L-lactide-coglycolide as microcapsules, microgranules or cylindrical implants containing dispersed dexpramipexole.

In further embodiments, pharmaceutical compositions including dexpramipexole or a pharmaceutically acceptable salt thereof may be formulated in rectal compositions such as suppositories or retention enemas, e.g., containing conventional suppository bases such as cocoa butter or other glycerides.

In some embodiments, pharmaceutical compositions including dexpramipexole or a pharmaceutically acceptable salt thereof may be formulated for transdermal administration. For example, such pharmaceutical compositions may be prepared to be applied to a plaster or applied by transdermal, therapeutic systems supplied to the subject. In other embodiments, pharmaceutical and therapeutic compositions including dexpramipexole or a pharmaceutically acceptable salt thereof for transdermal administration may include a suitable solid or gel phase carriers or excipients such as, but are not limited to, calcium carbonate, calcium phosphate, various sugars, starches, cellulose derivatives, gelatin, and polymers such as, e.g., polyethyleneglycols. In some embodiments, pharmaceutical compositions including dexpramipexole may be administered alone as a single therapeutic agent. In other embodiments, the pharmaceutical compositions including dexpramipexole may be administered in combination with one or more other active ingredients, such as, for example, adjuvants, protease inhibitors, or other compatible drugs or compounds where such a combination is seen to be desirable or advantageous in achieving the desired effects of the methods described herein.

The pharmaceutical compositions described herein may be prepared, packaged, or sold in bulk as a single unit dose or as multiple unit doses and may be administered in the conventional manner by any route where they are active. For example, the compositions may be administered orally, ophthalmically, intravenously, intramuscularly, intra-arterially, intramedullary, intrathecally, intraventricularly, transdermally, subcutaneously, intraperitoneally, intravesicularly, intranasally, enterally, topically, sublingually, rectally, by inhalation, by depot injections, or by implants or by use of vaginal creams, suppositories, pessaries, vaginal rings, rectal suppositories, intrauterine devices, and transdermal forms such as patches and creams. Specific modes of administration will depend on the indication. The selection of the specific route of administration and the dose regimen may be adjusted or titrated by the clinician according to known methods in order to obtain the optimal clinical response. All of the methods described herein may be carried out by administering dexpramipexole by any such route for administration described herein. Additionally, dexpramipexole may be delivered by using any such route of administration for all of the dosage regimens described herein. The compositions and amounts of non-active ingredients in such a composition may depend on the amount of the active ingredient, and on the size and shape of the tablet or capsule. Such parameters may be readily appreciated and understood by one of skill in the art.

In some embodiments, the pharmaceutical compounds may be formulated readily by combining these compounds with pharmaceutically acceptable carriers well known in the art. Such carriers enable the compounds to be formulated as tablets, pills, dragees, capsules, liquids, gels, syrups, slurries, suspensions and the like, for oral ingestion by a subject to be treated. Pharmaceutical preparations for oral use may be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethylcellulose, sodium carboxymethylcellulose, and polyvinylpyrrolidone (PVP). In some embodiments, disintegrating agents may be added, such as, but not limited to, the cross-linked polyvinyl pyrrolidone, agar, or alginic acid or a salt thereof such as sodium alginate.

In some embodiments, the pharmaceutical composition may include a diluent in an amount from about 20% to about 50% by weight of said composition; optionally, a second diluent in an amount from about 10% to about 30% by weight of said composition; optionally, a disintegrant in an amount from about 2% to about 6% of said composition; optionally, a lubricant in an amount from about 0.01% to about 2% of said composition; and dexpramipexole. In further embodiments, the pharmaceutical composition may include any amount or combination of microcrystalline cellulose, mannitol, croscarmellose sodium, crospovidone, croscarmellose magnesium stearate, or combination thereof. In some embodiments, the pharmaceutical composition may include microcrystalline cellulose, mannitol, croscarmellose sodium, magnesium stearate, or a combination thereof. In other embodiments, the pharmaceutical composition may include microcrystalline cellulose in an amount from about 20% to about 50% by weight of said composition; mannitol in an amount from about 10% to about 30% by weight of said composition; crospovidone in an amount from about 2% to about 6% of said composition; magnesium stearate in an amount from about 0.01% to about 2% of said composition; and dexpramipexole.

The pharmaceutical composition may have a chiral purity for dexpramipexole of at least 99.5%, preferably at least 99.6%, preferably at least 99.7%, preferably at least 99.8%, preferably at least 99.9%, preferably at least 99.95%, or more preferably at least 99.99%. In some embodiments, the chiral purity for dexpramipexole is 100%. In some embodiments, the composition has a chiral purity for dexpramipexole of 99.9% or greater. In some embodiments, the composition has a chiral purity for dexpramipexole of 99.95% or greater. In some embodiments, the composition has a chiral purity for dexpramipexole of 99.99% or greater. The high chiral purity of the pramipexole used herein, dexpramipexole, allows for therapeutic compositions that may have a wide individual and daily dose range.

The embodiments for amounts of dexpramipexole or a pharmaceutically acceptable salt thereof in the pharmaceutical composition, chiral purity, and dosage form, which are described herein separately for the sake of brevity, may be joined in any suitable combination.

In a further embodiment, a pharmaceutical composition may comprise a therapeutically effective amount of dexpramipexole or a pharmaceutically acceptable salt thereof and a NOAEL dose amount of (S)-pramipexole. The pharmaceutical composition may further comprise a pharmaceutically acceptable carrier and/or excipient. Such embodiments may further include one or more diluent, one or more disintegrant, one or more lubricant, one or more pigment or colorant, one or more gelatin, one or more plasticizer and the like.

In some embodiments, the NOAEL dose amount of (S)-pramipexole is less than about 1.50 mg. In other embodiments, the NOAEL dose amount of (S)-pramipexole is an amount that does not exceed about 1.0 mg. In certain embodiments, the NOAEL dose amount of (S)-pramipexole is an amount that does not exceed about 0.75 mg, about 0.5 mg, about 0.25 mg, about 0.125 mg or about 0.05 mg. In some embodiments, the NOAEL dose amount of (S)-pramipexole is less than about 0.5 mg, less than about 0.125 mg, or less than about 0.05 mg. In some embodiments, the therapeutically effective amount of dexpramipexole and a NOAEL amount of (S)-pramipexole are administered in a single unit dose form.

Embodiments of the invention are not limited to any particular agent encompassed by the classes of agents described above, and any agent that falls within any of these categories may be utilized in embodiments of the invention. Non-limiting examples of such agents are provided for clarity. Any of the secondary agents described above may be useful in embodiments of the invention.

The embodiments for disease states, subject type, daily dose amounts, therapeutically effective amounts, no observable adverse effect level dose amounts, non-effective dose amounts, pharmaceutical compositions, and chiral purities for the methods of the invention, which are described herein separately for the sake of brevity, can be joined in any suitable combination.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using "consisting of" or "consisting essentially of" language, rather than "comprising". When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Example 1

Effects of Dexpramipexole on Minipig Eosinophils

In a 39-week repeat-dose toxicology study, minipigs were dosed at 0, 7.5, 25, and 75 mg/kg dexpramipexole by daily oral gavage through Study Day 45 and at 0, 7.5, 25, and 50 mg/kg dexpramipexole from Study Day 46 to study completion. As shown in FIG. 1, dexpramipexole produced both a dose- and time-dependent reduction in eosinophils. The effects of dexpramipexole treatment on minipig eosinophils was statistically significant at 39 weeks in the 25 mg/kg group and at all time points in the 50/75 mg/kg group. These differences were not considered adverse from a safety perspective.

Example 2

Eosinophil and Basophil Reductions in a Phase 2 Trial in ALS Subjects

In a Phase 2 trial in ALS, a dose- and time-dependent decrease in eosinophil counts was seen among subjects receiving dexpramipexole treatment. The Phase 2 trial was a two-part, double-blind study that evaluated the safety, tolerability, and clinical effects of dexpramipexole in ALS patients.

Figure 2A:
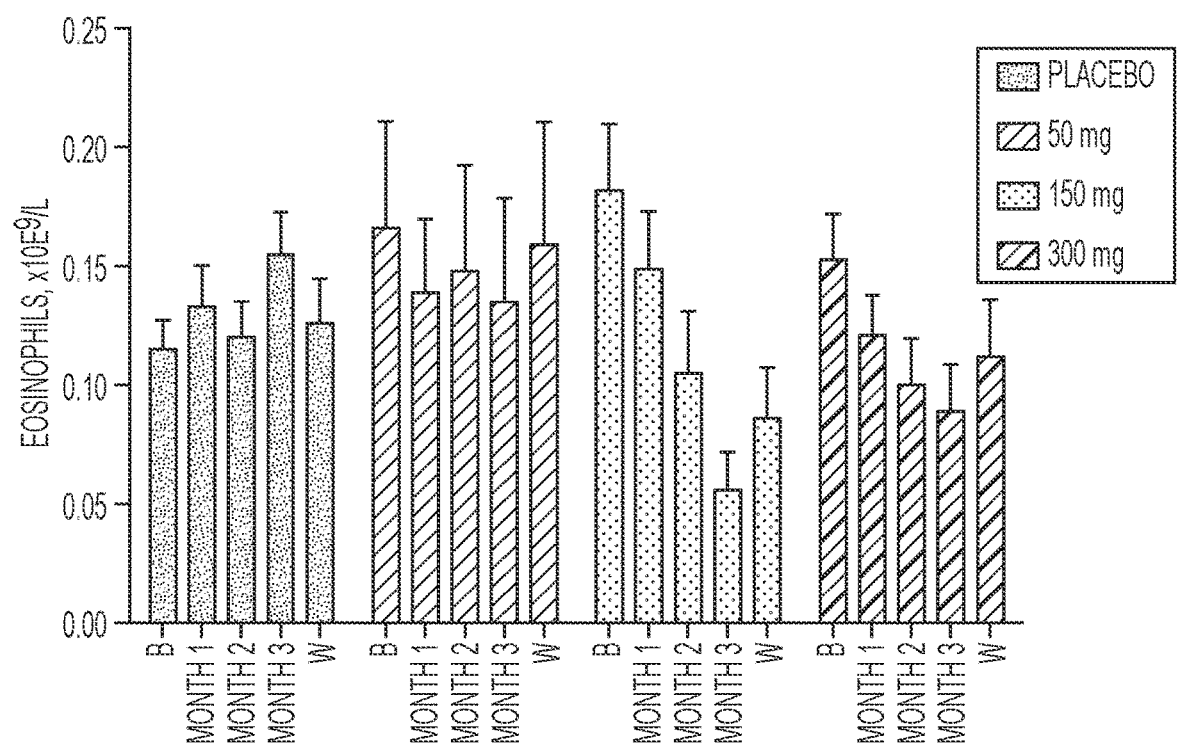
FIG. 2A depicts the dose-dependent effect of dexpramipexole on eosinophil counts in the Phase 2 trial CL201 (n=22-25 per group).

In Part 1, subjects were randomized to placebo (n=27), 50 mg/day (n=23), 150 mg/day (n=26), or 300 mg/day dexpramipexole (n=26) for 12 weeks. From baseline to week 12, mean serum eosinophils increased by 29.2% in the placebo group and declined by 18.2% ($p=0.0370$), 69.9%, ($p<0.0001$), and 42.9% ($p=0.0008$) in the 50 mg, 150 mg, and 300 mg groups, respectively (FIG. 2A).

During a one-month washout following week 12, mean eosinophils at week 16 recovered to 47% and 73% of baseline levels in the 150 and 300 mg/day groups, respectively.

Following drug washout, subjects in part 2 re-randomized to 150 mg twice daily had a greater decline in eosinophils from week 16 to week 40 than subjects re-randomized to 25 mg twice daily (78.9% vs 17.6%, $p=0.011$).

Example 3

Eosinophil-Lowering and Basophil-Lowering Effects of Dexpramipexole in a Phase 3 Trial The phase 3 clinical trial was a double-blind study of dexpramipexole in ALS patients randomized 1:1 to placebo or dexpramipexole 300 mg daily treatment. Hematology parameters were collected as part of routine safety monitoring. Eosinophil and basophil counts were retrospectively analyzed by visit.

Eosinophil levels were summarized over available time points and analyzed by ANOVA testing the effect of treatment vs. placebo on mean changes in serum eosinophil counts from baseline. Subjects with baseline eosinophils from 0 to $0.02 \times 10^9$/L (constituting less than 2% of all subjects analyzed) were censored from the primary analysis because of the inherent limitation to observe a decline from baseline.

Figure 2B:
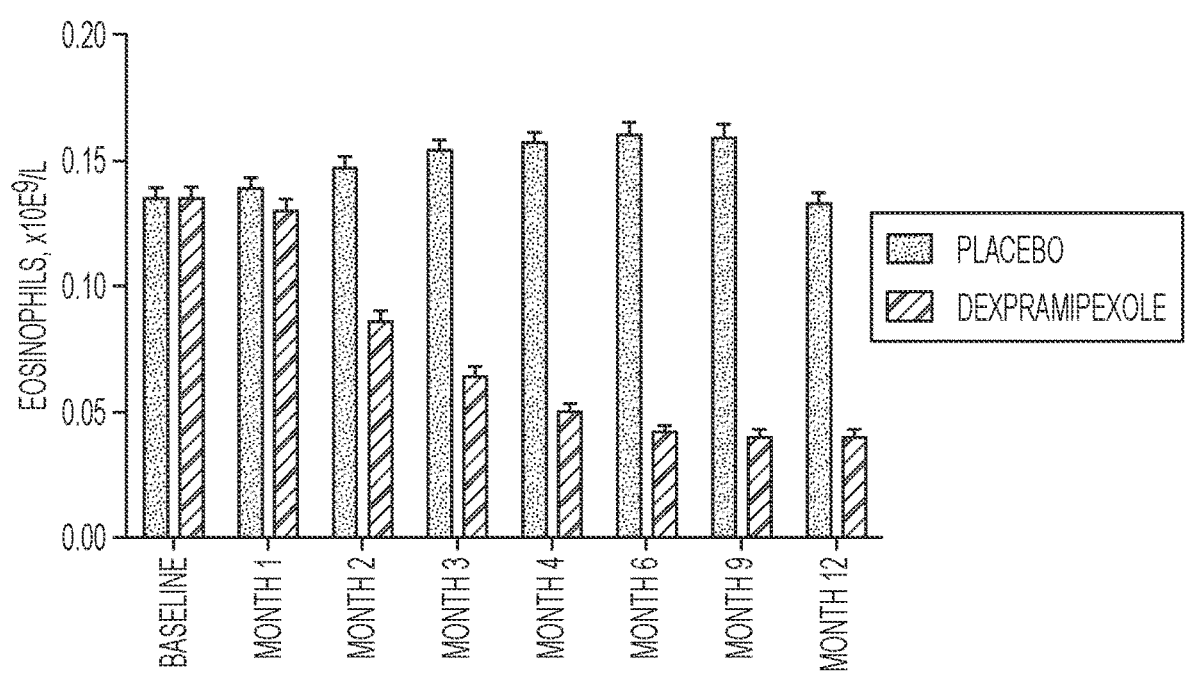
FIG. 2B depicts the time-dependent effect of dexpramipexole on eosinophil counts in the Phase 3 trial EMPOWER. (Mean±SEM, N=474 at baseline, N=328 at 12 months in dexpramipexole group, 467 and 340 in placebo group).

The eosinophil-lowering effect developed slowly, reached plateau at about month 4, and persisted through month 12 (FIG. 2B). A profound decrease in peripheral blood eosinophil count was observed after 8-12 weeks of treatment with dexpramipexole that persisted for the duration of the trial. Statistical analysis of the change from baseline was performed at month 6 to remove the effect of study dropouts in later months. At this time point, mean eosinophil counts were 68.4% reduced from baseline ($p<0.0001$).

The effect of dexpramipexole in reducing eosinophil counts was observed in most patients, with 77.5% of dexpramipexole-treated subjects experiencing a 50% or greater decline in eosinophil count after 6 months of treatment.

ALS is not typically associated with a systemic inflammatory response and accordingly baseline eosinophil counts in the dexpramipexole-treated and placebo groups of 0.129 and $0.127 \times 10^9$/L, respectively, were within the reference range. However, the eosinophil-lowering effect of dexpramipexole was not diminished in subjects (n=42) with higher eosinophil counts (i.e. $>0.25 \times 10^9$/L), among whom a 75% decrease was observed after 6 months of treatment (data not shown).

Figure 3A:
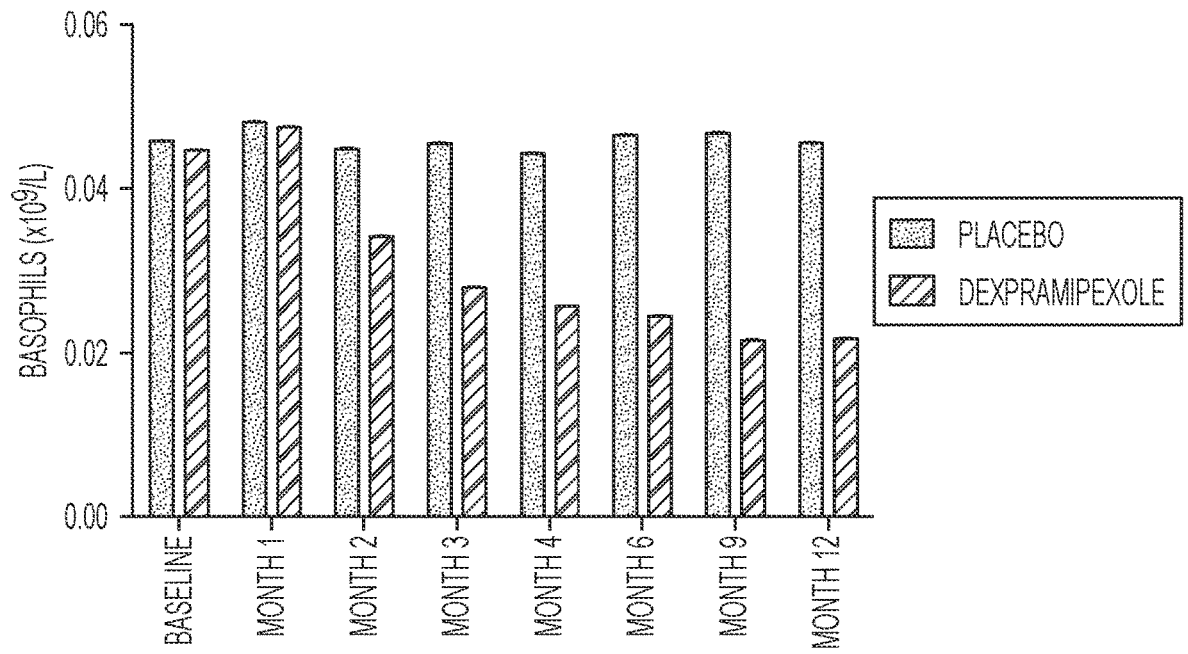
FIG. 3A depicts the time-dependent effects of dexpramipexole on basophils in the Phase 3 trial.
Figure 3B:
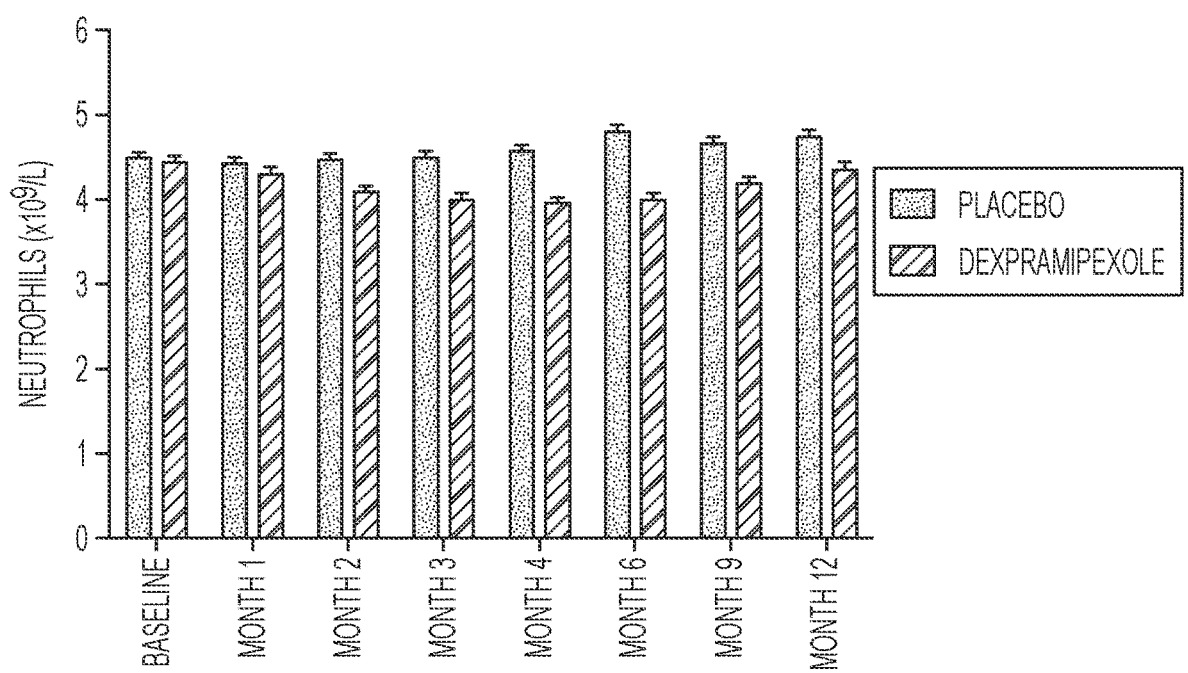
FIG. 3B depicts the effects of dexpramipexole on neutrophils in the Phase 3 trial. (Mean±SEM, N=474 at baseline in dexpramipexole group, 468 in placebo group).

Changes in basophil counts were also analyzed in the Phase 3 trial. As shown in FIG. 3A, basophil counts, like eosinophil counts, declined slowly, reached plateau at about month 4, and remained reduced for the duration of treatment through month 12. At the six month analysis, mean basophil counts were 45.5% reduced from baseline (p<0.0001).

Example 4

Figure 4A:
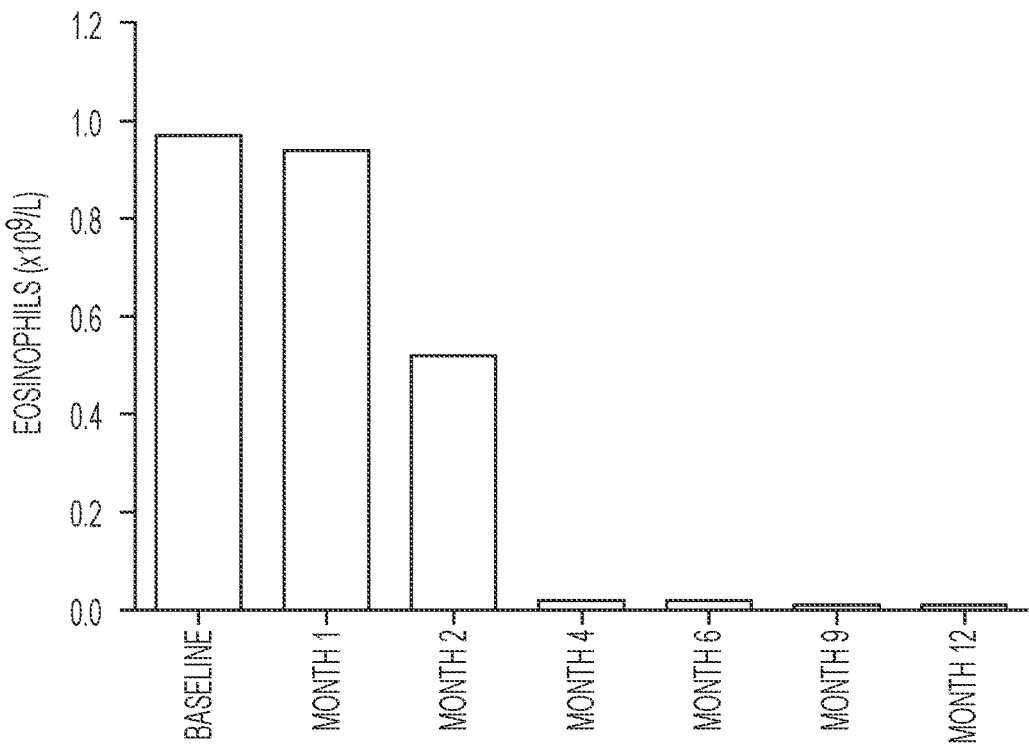
FIG. 4A shows that dexpramipexole decreases eosinophils in a subject in the Phase 2 study with a high baseline eosinophil count.

Effects of Dexpramipexole on ALS Clinical Trial Subjects with Baseline Hypereosinophilia Baseline parameters were reviewed in Phase 2 and Phase 3 studies of dexpramipexole in ALS to identify subjects with significantly elevated eosinophil counts prior to the initiation of dexpramipexole treatment. As shown in FIG. 4A, one Phase 2 subject with hypereosinophilia at Part 2 baseline showed a decrease in eosinophil counts with dexpramipexole treatment. The substantial reduction in eosinophils persisted for the period the subject remained on dexpramipexole through month 12.

Figure 4B:
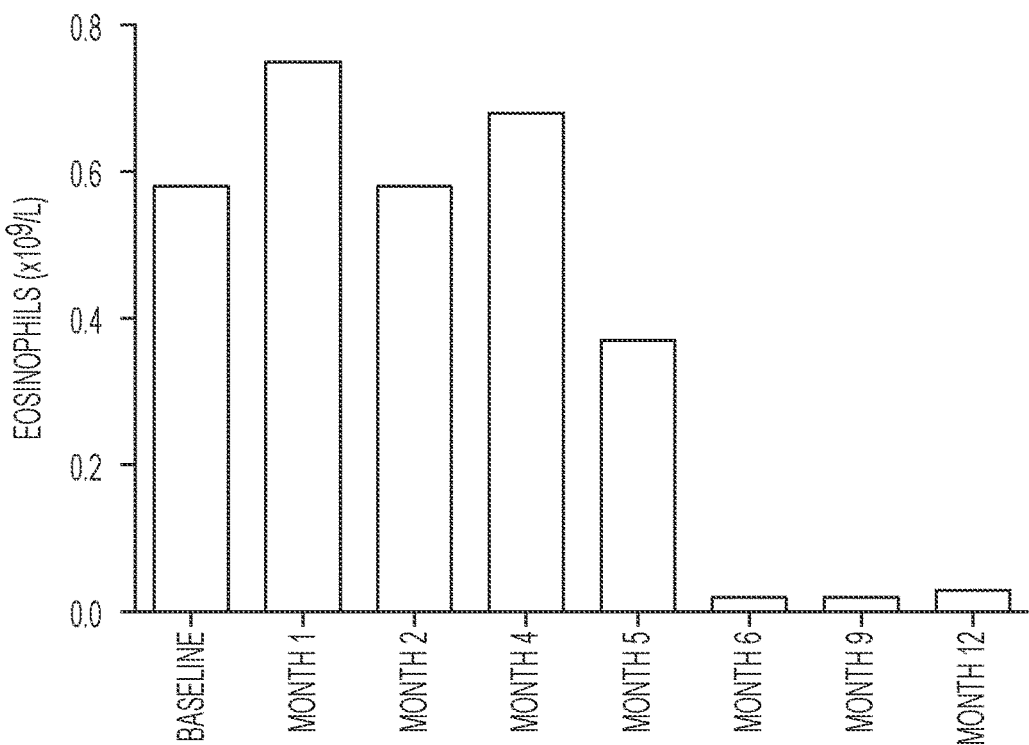
FIG. 4B shows that dexpramipexole decreases eosinophils in a subject in the Phase 3 trial with a high baseline eosinophil count.

As shown in FIG. 4B, a Phase 3 subject with elevated eosinophil counts at baseline also showed a decrease in eosinophil counts with dexpramipexole treatment. This subject had the highest baseline eosinophil count in the dexpramipexole treatment group in the Phase 3 study and showed a decrease in eosinophil counts on treatment. The substantial reduction in eosinophils persisted for the period the subject remained on dexpramipexole through month 12.

Example 5

Hematological Effects of Dexpramipexole

Hematological parameters were measured in a Phase 3 study of dexpramipexole in ALS. Because of the high rate of mortality among ALS patients, including subjects in the Phase 3 trial, hematology parameters obtained at the month 6 visit were chosen for analysis to remove the effect of study dropouts in later months. At month 6 in the Phase 3 study, all myeloid and lymphoid cell types measured showed statistically significant mean reductions from baseline, although the magnitude of the effect was greatest for eosinophils, which declined 68.4% from baseline, and basophils, which declined 45.5% from baseline (FIG. 5). Notably among hematology parameters, there was no effect of dexpramipexole on either red blood cells or platelets compared to the control group.

Example 6

Effect of Dexpramipexole in a Mouse Model of Asthma

Allergic asthma is a condition initiated by an immune response to a diverse array of allergens and is manifested by airway obstruction, hyper-reactivity, and lung inflammation. This asthmatic response can be mimicked in experimental animals by exposing them to an array of antigens. Like the asthmatic response in humans, the animal model of pulmonary inflammation is characterized by an extensive inflammatory response, including a localized increase in cellular infiltrate and inflammatory cytokines.

A study was conducted to assess the effects of dexpramipexole in this model. Female 6- to 8-week-old C57BL/6 mice were untreated (Unt), treated with ovalbumin (OVA), with OVA and 30 or 100 mg/kg dexpramipexole, or dexpramipexole alone. Whole blood was collected from each mouse at day zero (prior to dosing), day 28 (14 days after initial OVA sensitization), and day 42 (after final OVA challenge). Samples were quantitated on a hemoanalyzer for number of cells in each subpopulation listed.

Figure 6:
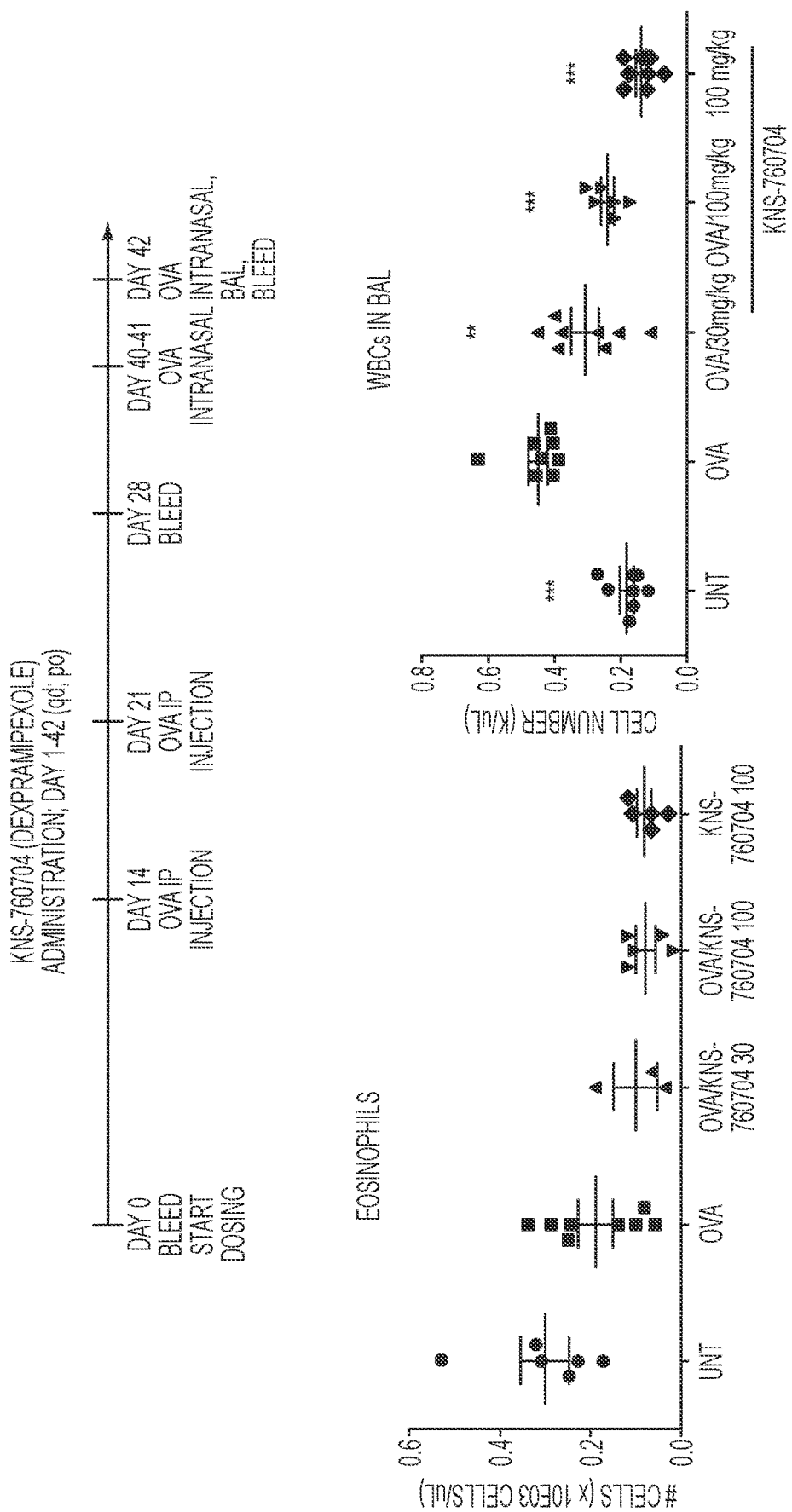
FIG. 6 depicts the effects of dexpramipexole in an ovalabumin pulmonary inflammation mouse model.

As shown in FIG. 6, at the end of the study (day 42), circulating levels of eosinophils were significantly reduced (p=0.0041) in the 100 mg/kg dose group compared to vehicle-treated controls. This result demonstrated that the mouse is a responsive animal model species as the circulating eosinophils were lowered by dexpramipexole treatment similar to minipig and humans.

In this model, the influx of white blood cells (WBCs) to the lungs is dominated by eosinophils, according to Nials and Uddin, Disease Models & Mechanisms 1, 213-220 (2008). Bronchoalveolar lavage fluid collected at the end of the experiment (day 42) showed a significant increase in infiltrating white blood cells in OVA-treated mice. Samples were quantitated on a hemoanalyzer for number of white blood cells. Treatment with dexpramipexole at 30 and 100 mg/kg caused a dose-dependent decrease in infiltrating white blood cells. (*p<0.001, p<0.01 compared to OVA, one-way ANOVA with post-hoc Dunnett's test).

What is claimed is:

1. A method of treating moderate to severe eosinophilic asthma in a human in need thereof comprising orally administering to the human a therapeutically effective amount of dexpramipexole, or a pharmaceutically acceptable salt thereof, wherein the therapeutically effective amount of dexpramipexole, or a pharmaceutically acceptable salt thereof, is about 50 milligrams to about 600 milligrams per day and wherein eosinophilic asthma is characterized by 150 eosinophil cells or more per microliter in peripheral blood prior to administering dexpramipexole, and wherein the moderate to severe eosinophilic asthma is treated in the human.

2. The method of claim 1, wherein the eosinophilic asthma is moderate.

3. The method of claim 1, wherein the eosinophilic asthma is severe.

4. The method of claim 1, wherein the pharmaceutically acceptable salt is (6R)-4, 5, 6, 7-tetrahydro-N6-propyl-2,6-benzothiazolediamine dihydrochloride monohydrate.

5. The method of claim 1, wherein the therapeutically effective amount of dexpramipexole, or a pharmaceutically acceptable salt thereof, is about 75 milligrams per day.

6. The method of claim 1, wherein the therapeutically effective amount of dexpramipexole, or a pharmaceutically acceptable salt thereof, is about 150 milligrams per day.

7. The method of claim 1, wherein the therapeutically effective amount of dexpramipexole, or a pharmaceutically acceptable salt thereof, is about 300 milligrams per day.

8. The method of claim 1, wherein the dexpramipexole or a pharmaceutically acceptable salt thereof is orally administered in a solid unit dose.

9. The method of claim 1, wherein administering comprises administering half of the daily dose twice per day.

10. The method of claim 5, wherein administering comprises administering half of the daily dose twice per day.

11. The method of claim 6, wherein administering comprises administering half of the daily dose twice per day.

12. The method of claim 7, wherein administering comprises administering half of the daily dose twice per day.

13. The method of claim 1 further comprising administering a second therapeutic agent.

14. The method of claim 13, wherein the second therapeutic agent is a corticosteroid.

15. The method of claim 1, wherein treatment results in a decrease in eosinophil levels in the lungs.

16. The method of claim 1, wherein treatment results in a decrease in eosinophil levels in the lower respiratory airways.

17. A method of treating eosinophilic asthma in a human in need thereof comprising orally administering to the human a therapeutically effective amount of dexpramipexole, or a pharmaceutically acceptable salt thereof, wherein the therapeutically effective amount of dexpramipexole, or a pharmaceutically acceptable salt thereof, is about 50 milligrams to about 600 milligrams per day and wherein eosinophilic asthma is characterized by 150 eosinophil cells or more per microliter in peripheral blood prior to administering dexpramipexole, and wherein the eosinophilic asthma is treated in the human.

18. The method of claim 17, wherein the pharmaceutically acceptable salt is (6R)-4, 5, 6, 7-tetrahydro-N6-propyl-2,6-benzothiazolediamine dihydrochloride monohydrate.

19. The method of claim 17, wherein the therapeutically effective amount of dexpramipexole, or a pharmaceutically acceptable salt thereof, is about 75 milligrams per day.

20. The method of claim 17, wherein the therapeutically effective amount of dexpramipexole, or a pharmaceutically acceptable salt thereof, is about 150 milligrams per day.

21. The method of claim 17, wherein the therapeutically effective amount of dexpramipexole, or a pharmaceutically acceptable salt thereof, is about 300 milligrams per day.

22. The method of claim 17, wherein the dexpramipexole or a pharmaceutically acceptable salt thereof is orally administered in a solid unit dose.

23. The method of claim 17, wherein administering comprises administering half of the daily dose twice per day.

24. The method of claim 19, wherein administering comprises administering half of the daily dose twice per day.

25. The method of claim 20, wherein administering comprises administering half of the daily dose twice per day.

26. The method of claim 21, wherein administering comprises administering half of the daily dose twice per day.

27. The method of claim 17 further comprising administering a second therapeutic agent.

28. The method of claim 27, wherein the second therapeutic agent is a corticosteroid.

29. The method of claim 17, wherein treatment results in a decrease in eosinophil levels in the lungs.

30. The method of claim 17, wherein treatment results in a decrease in eosinophil levels in the lower respiratory airways.

31. The method of claim 1, wherein administering comprises administering the daily dose once per day.

32. The method of claim 5, wherein administering comprises administering the daily dose once a per day.

33. The method of claim 6, wherein administering comprises administering the daily dose once per day.

34. The method of claim 7, wherein administering comprises administering the daily dose once per day.

35. The method of claim 17, wherein administering comprises administering the daily dose once per day.

36. The method of claim 19, wherein administering comprises administering the daily dose once per day.

37. The method of claim 20, wherein administering comprises administering the daily dose once per day.

38. The method of claim 21, wherein administering comprises administering the daily dose once per day.

39. The method of claim 2, wherein the pharmaceutically acceptable salt is (6R)-4, 5, 6, 7-tetrahydro-N6-propyl-2,6-benzothiazolediamine dihydrochloride monohydrate.

40. The method of claim 2, wherein the therapeutically effective amount of dexpramipexole, or a pharmaceutically acceptable salt thereof, is about 75 milligrams per day.

41. The method of claim 2, wherein the therapeutically effective amount of dexpramipexole, or a pharmaceutically acceptable salt thereof, is about 150 milligrams per day.

42. The method of claim 2, wherein the therapeutically effective amount of dexpramipexole, or a pharmaceutically acceptable salt thereof, is about 300 milligrams per day.

43. The method of claim 2, wherein the dexpramipexole or a pharmaceutically acceptable salt thereof is orally administered in a solid unit dose.

44. The method of claim 2, wherein administering comprises administering half of the daily dose twice per day.

45. The method of claim 40, wherein administering comprises administering half of the daily dose twice per day.

46. The method of claim 41, wherein administering comprises administering half of the daily dose twice per day.

47. The method of claim 42, wherein administering comprises administering half of the daily dose twice per day.

48. The method of claim 2 further comprising administering a second therapeutic agent.

49. The method of claim 48, wherein the second therapeutic agent is a corticosteroid.

50. The method of claim 2, wherein treatment results in a decrease in eosinophil levels in the lungs.

51. The method of claim 2, wherein treatment results in a decrease in eosinophil levels in the lower respiratory airways.

52. The method of claim 2, wherein administering comprises administering the daily dose once a per day.

53. The method of claim 40, wherein administering comprises administering the daily dose once per day.

54. The method of claim 41, wherein administering comprises administering the daily dose once per day.

55. The method of claim 42, wherein administering comprises administering the daily dose once per day.

56. The method of claim 3, wherein the pharmaceutically acceptable salt is (6R)-4, 5, 6, 7-tetrahydro-N6-propyl-2,6-benzothiazolediamine dihydrochloride monohydrate.

57. The method of claim 3, wherein the therapeutically effective amount of dexpramipexole, or a pharmaceutically acceptable salt thereof, is about 75 milligrams per day.

58. The method of claim 3, wherein the therapeutically effective amount of dexpramipexole, or a pharmaceutically acceptable salt thereof, is about 150 milligrams per day.

59. The method of claim 3, wherein the therapeutically effective amount of dexpramipexole, or a pharmaceutically acceptable salt thereof, is about 300 milligrams per day.

60. The method of claim 3, wherein the dexpramipexole or a pharmaceutically acceptable salt thereof is orally administered in a solid unit dose.

61. The method of claim 3, wherein administering comprises administering half of the daily dose twice per day.

62. The method of claim 57, wherein administering comprises administering half of the daily dose twice per day.

63. The method of claim 58, wherein administering comprises administering half of the daily dose twice per day.

64. The method of claim 59, wherein administering comprises administering half of the daily dose twice per day.

65. The method of claim 3 further comprising administering a second therapeutic agent.

66. The method of claim 65, wherein the second therapeutic agent is a corticosteroid.

67. The method of claim 3, wherein treatment results in a decrease in eosinophil levels in the lungs.

68. The method of claim 3, wherein treatment results in a decrease in eosinophil levels in the lower respiratory airways.

69. The method of claim 3, wherein administering comprises administering the daily dose once per day.

70. The method of claim 57, wherein administering comprises administering the daily dose once a per day.

71. The method of claim 58, wherein administering comprises administering the daily dose once per day.

72. The method of claim 59, wherein administering comprises administering the daily dose once per day.

73. The method of claim 1, wherein eosinophilic asthma is characterized by about 300 eosinophil cells or more per microliter in the peripheral blood prior to administering dexpramipexole.

74. The method of claim 73, wherein eosinophilic asthma is characterized by about 400 eosinophil cells or more per microliter in the peripheral blood prior to administering dexpramipexole.

75. The method of claim 74, wherein eosinophilic asthma is characterized by about 500 eosinophil cells or more per microliter in the peripheral blood prior to administering dexpramipexole.

76. The method of claim 75, wherein eosinophilic asthma is characterized by about 1000 eosinophil cells or more per microliter in the peripheral blood prior to administering dexpramipexole.

77. The method of claim 76, wherein eosinophilic asthma is characterized by about 1500 eosinophil cells or more per microliter in the peripheral blood prior to administering dexpramipexole.

78. The method of claim 17, wherein eosinophilic asthma is characterized by about 300 eosinophil cells or more per microliter in the peripheral blood prior to administering dexpramipexole.

79. The method of claim 78, wherein eosinophilic asthma is characterized by about 400 eosinophil cells or more per microliter in the peripheral blood prior to administering dexpramipexole.

80. The method of claim 79, wherein eosinophilic asthma is characterized by about 500 eosinophil cells or more per microliter in the peripheral blood prior to administering dexpramipexole.

81. The method of claim 80, wherein eosinophilic asthma is characterized by about 1000 eosinophil cells or more per microliter in the peripheral blood prior to administering dexpramipexole.

82. The method of claim 81, wherein eosinophilic asthma is characterized by about 1500 eosinophil cells or more per microliter in the peripheral blood prior to administering dexpramipexole.

83. The method of claim 1, wherein the eosinophil cells in the peripheral blood in the human are reduced by at least 50% compared to prior to administering dexpramipexole.

84. The method of claim 83, wherein the eosinophil cells in the peripheral blood in the human are reduced by at least 60% compared to prior to administering dexpramipexole.

85. The method of claim 84, wherein the eosinophil cells in the peripheral blood in the human are reduced by at least 70% compared to prior to administering dexpramipexole.

86. The method of claim 85, wherein the eosinophil cells in the peripheral blood in the human are reduced by at least 80% compared to prior to administering dexpramipexole.

87. The method of claim 86, wherein the eosinophil cells in the peripheral blood in the human are reduced by at least 90% compared to prior to administering dexpramipexole.

88. The method of claim 17, wherein the eosinophil cells in the peripheral blood in the human are reduced by at least 50% compared to prior to administering dexpramipexole.

89. The method of claim 88, wherein the eosinophil cells in the peripheral blood in the human are reduced by at least 60% compared to prior to administering dexpramipexole.

90. The method of claim 89, wherein the eosinophil cells in the peripheral blood in the human are reduced by at least 70% compared to prior to administering dexpramipexole.

91. The method of claim 90, wherein the eosinophil cells in the peripheral blood in the human are reduced by at least 80% compared to prior to administering dexpramipexole.

92. The method of claim 91, wherein the eosinophil cells in the peripheral blood in the human are reduced by at least 90% compared to prior to administering dexpramipexole.

93. The method of claim 2, wherein administering comprises administering one third of the daily dose three times per day.

94. The method of claim 40, wherein administering comprises administering one third of the daily dose three times per day.

95. The method of claim 41, wherein administering comprises administering one third of the daily dose three times per day.

96. The method of claim 42, wherein administering comprises administering one third of the daily dose three times per day.

97. The method of claim 3, wherein administering comprises administering one third of the daily dose three times per day.

98. The method of claim 57, wherein administering comprises administering one third of the daily dose three times per day.

99. The method of claim 58, wherein administering comprises administering one third of the daily dose three times per day.

100. The method of claim 59, wherein administering comprises administering one third of the daily dose three times per day.

101. The method of claim 2, wherein administering comprises administering one fourth of the daily dose four times per day.

102. The method of claim 40, wherein administering comprises administering one fourth of the daily dose four times per day.

103. The method of claim 41, wherein administering comprises administering one fourth of the daily dose four times per day.

104. The method of claim 42, wherein administering comprises administering one fourth of the daily dose four times per day.

105. The method of claim 3, wherein administering comprises administering one fourth of the daily dose four times per day.

106. The method of claim 57, wherein administering comprises administering one fourth of the daily dose four times per day.

107. The method of claim 58, wherein administering comprises administering one fourth of the daily dose four times per day.

108. The method of claim 59, wherein administering comprises administering one fourth of the daily dose four times per day.

109. The method of claim 2, wherein administering comprises administering one fifth of the daily dose five times per day.

110. The method of claim 40, wherein administering comprises administering one fifth of the daily dose five times per day.

111. The method of claim 41, wherein administering comprises administering one fifth of the daily dose five times per day.

112. The method of claim 42, wherein administering comprises administering one fifth of the daily dose five times per day.

113. The method of claim 3, wherein administering comprises administering one fifth of the daily dose five times per day.

114. The method of claim 57, wherein administering comprises administering one fifth of the daily dose five times per day.

115. The method of claim 58, wherein administering comprises administering one fifth of the daily dose five times per day.

116. The method of claim 59, wherein administering comprises administering one fifth of the daily dose five times per day.

117. The method of claim 2, wherein the therapeutically effective amount of dexpramipexole, or a pharmaceutically acceptable salt thereof, is in a range between about 50 milligrams per day to about 300 milligrams per day.

118. The method of claim 2, wherein the therapeutically effective amount of dexpramipexole, or a pharmaceutically acceptable salt thereof, is in a range between about 100 milligrams per day to about 600 milligrams per day.

119. The method of claim 2, wherein the therapeutically effective amount of dexpramipexole, or a pharmaceutically acceptable salt thereof, is in a range between about 150 milligrams per day to about 300 milligrams per day.

120. The method of claim 2, wherein the therapeutically effective amount of dexpramipexole, or a pharmaceutically acceptable salt thereof, is in a range between about 150 milligrams per day to about 600 milligrams per day.

121. The method of claim 2, wherein the therapeutically effective amount of dexpramipexole, or a pharmaceutically acceptable salt thereof, is in a range between about 300 milligrams per day to about 500 milligrams per day.

122. The method of claim 2, wherein the therapeutically effective amount of dexpramipexole, or a pharmaceutically acceptable salt thereof, is in a range between about 300 milligrams per day to about 600 milligrams per day.

123. The method of claim 3, wherein the therapeutically effective amount of dexpramipexole, or a pharmaceutically acceptable salt thereof, is in a range between about 50 milligrams per day to about 300 milligrams per day.

124. The method of claim 3, wherein the therapeutically effective amount of dexpramipexole, or a pharmaceutically acceptable salt thereof, is in a range between about 100 milligrams per day to about 600 milligrams per day.

125. The method of claim 3, wherein the therapeutically effective amount of dexpramipexole, or a pharmaceutically acceptable salt thereof, is in a range between about 150 milligrams per day to about 300 milligrams per day.

126. The method of claim 3, wherein the therapeutically effective amount of dexpramipexole, or a pharmaceutically acceptable salt thereof, is in a range between about 150 milligrams per day to about 600 milligrams per day.

127. The method of claim 3, wherein the therapeutically effective amount of dexpramipexole, or a pharmaceutically acceptable salt thereof, is in a range between about 300 milligrams per day to about 500 milligrams per day.

128. The method of claim 3, wherein the therapeutically effective amount of dexpramipexole, or a pharmaceutically acceptable salt thereof, is in a range between about 300 milligrams per day to about 600 milligrams per day.

* * * * *